United States Patent
Robinson et al.

(10) Patent No.: US 7,091,313 B2
(45) Date of Patent: Aug. 15, 2006

(54) SYNTHESIS OF TEMPLATE-FIXED β-HAIRPIN LOOP MIMETICS

(75) Inventors: John A. Robinson, Zürich (CH); Daniel Obrecht, Basel (CH)

(73) Assignees: Universitat Zurich, Zurich (CH); Polyphor AG, Allschwil (CH)

( * ) Notice: Subject to any disclaimer, the term of this patent is extended or adjusted under 35 U.S.C. 154(b) by 107 days.

(21) Appl. No.: 11/029,331

(22) Filed: Jan. 5, 2005

(65) Prior Publication Data

US 2005/0181454 A1    Aug. 18, 2005

Related U.S. Application Data

(62) Division of application No. 10/070,217, filed as application No. PCT/EP99/06369 on Aug. 30, 1999, now Pat. No. 6,878,804.

(51) Int. Cl.
*A61K 38/00* (2006.01)

(52) U.S. Cl. .................. 530/333; 530/317; 530/311

(58) Field of Classification Search ............ 530/317, 530/333, 311, 313, 321, 329
See application file for complete search history.

(56) References Cited

U.S. PATENT DOCUMENTS 5,670,155 A    9/1997    Kahn

FOREIGN PATENT DOCUMENTS

EP    0592791 A2    4/1994

OTHER PUBLICATIONS

S. Hanessian, et al., "Design and Synthesis of Conformationally Constrained Amino Acids as Versatile Scaffolds and Peptide Mimetics", Tetrahedron Report No. 426, *Tetrahedron*, vol. 53, No. 38, pp. 12789-12854, Elseview Science Ltd., 1997.

D. Obrecht, et al., "Novel Peptide Mimetic Building Blocks and Strategies for Efficient Lead Finding", *Advances in Medicinal Chemistry*, vol. 4, pp. 1-68, JAI Press Inc., 1999.

J. Späth, et al., "Stabilization of a β-Hairpin Conformation in a Cyclic Peptide Using the Templating Effect of a Hetrochiral Diproline Unit", *Helvetica Chimica Institute*, vol. 81, XP-002137025, Organic Chemistry, University of Zürich, 1998.

M. E. Pfeifer, et al., "Stabilisation of β-hairpin conformations in a protein surface mimetic using a bicyclic template derived from (2S,3R,4R)-diaminoproline", *Chem. Commun.*, pp. 1977-1978, XP-002137024, Institute of Organic Chemistry, University of Zurich, 1998.

K. Sato, et al., "Solid phase synthesis of human growth hormone-releasing factor analogs containing a bicyclic β-turn dipeptide", *International Journal of Peptide & Protein Research*, pp. 340-345, XP-002292090, 1991.

M. Favre, et al., "Structural Mimicry of Canonical Conformations in Antibody Hypervariable Loops Using Cyclic Peptides Containing a Heterochiral Diproline Template", *J. Am. Chem. Soc.*, 121, pp. 2679-2685, XP-002137023, 1999.

*Primary Examiner*—Robert A. Wax
*Assistant Examiner*—Robert B. Mondesi
(74) *Attorney, Agent, or Firm*—Hoffman & Baron, LLP

(57) ABSTRACT

Template-fixed β-hairpin loop mimetics comprising a template corresponding to one of the structures (a), (b), (c), (d), (e), (f), (g), (h) and a template-fixed chain of 4 to 20 α-amino acid residues which, if their α-C atom is asymmetric, have L-configuration can be manufactured by a novel process which is based on a mixed solid- and solution phase synthetic strategy. If desired, this process can be modified to give the enantiomers of these template-fixed β-hairpin loop mimetics. These enantiomers are novel compounds, and many of said template-fixed β-hairpin loop mimetics themselves are also novel compounds. The template-fixed β-hairpin loop mimetics and their enantiomers can mimic flat surfaces of proteins and thus be used to probe large surface protein-protein interactions. Accordingly they can serve as lead finding tools for protein targets where it is difficult to find small-molecular-weight lead compounds.

12 Claims, 1 Drawing Sheet

SYNTHESIS OF TEMPLATE-FIXED β-HAIRPIN LOOP MIMETICS

CROSS-REFERENCE TO RELATED APPLICATIONS

The present application is a divisional of U.S. application Ser. No. 10/070,217, filed Feb. 26, 2002, now U.S. Pat. No. 6,878,804, which is the National Stage filing of PCT/EP99/06369 under 35 U.S.C. §371 filed Aug. 30, 1999.

The present invention relates to a reliable process for the synthesis of template-fixed β-hairpin loop mimetics of the general formula

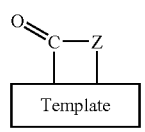

I wherein

Z is a chain of n α-amino acid residues which, if their α-C atom is asymmetric, have L-configuration, n being an integer from 4 to 20, the positions of said amino acid residues in said chain being counted starting from the N-terminal amino acid;

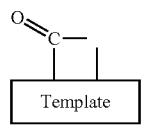

is one of the groups of formulae

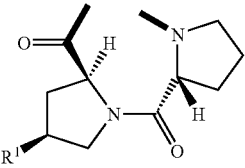

(a)

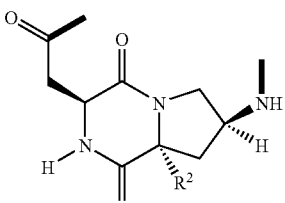

(b)

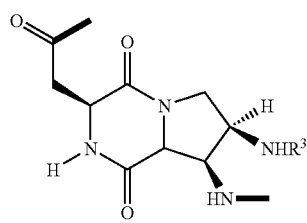

(c)

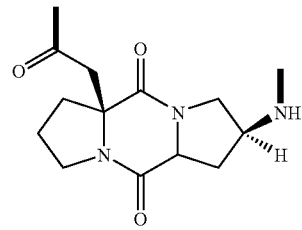

(d)

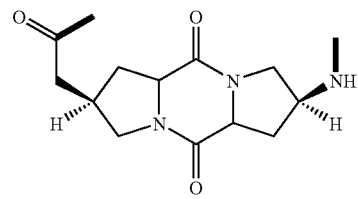

(e)

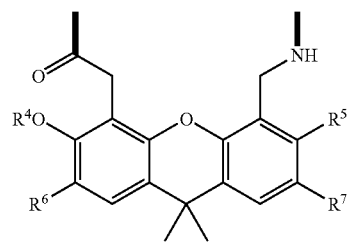

(f)

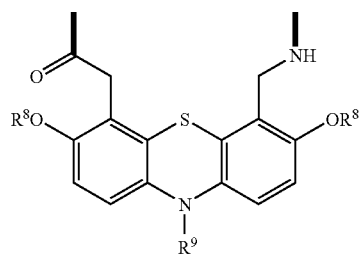

(g)

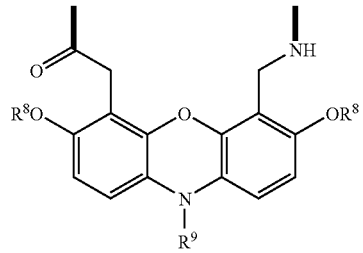

(h)

$R^1$ is hydrogen or a protected amino group;
$R^2$ is hydrogen or a group of formula $CH_2$—$COOR^{10}$;
$R^3$ is an amino-protecting group;
$R^4$ is lower alkyl or aryl-lower alkyl;
$R^5$ is lower alkyl, lower alkoxy or aryl;
$R^6$ is hydrogen, lower alkyl, substituted lower alkyl, aryl Br or $NO_2$;
$R^7$ is hydrogen, lower alkyl, substituted lower alkyl, aryl Br or $NO_2$;
$R^8$ is lower alkyl substituted lower alkyl or aryl-lower alkyl;
$R^9$ is lower alkyl, substituted lower alkyl or aryl-lower alkyl; and
$R^{10}$ is hydrogen, lower alkyl, substituted lower alkyl aryl, aryl-lower alkyl, aroyl-lower alkyl or allyl;

and of salts thereof.

This process is based on a mixed solid- and solution phase synthetic strategy and comprises (a) coupling an appropriately functionalized solid support with an appropriately N-protected derivative of that amino acid which in the desired end-product is in position n/2, n/2+1 or n/2−1 if n is an even number and, respectively, in position n/2+1/2 or n/2−1/2 if n is an odd number, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating, if necessary, steps (c) and (d) until the N-terminal amino acid residue has been introduced;

(f) coupling the product thus obtained with a compound of the general formula

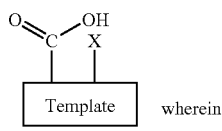

wherein

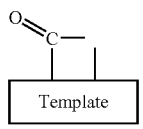

is to be group (a), above, alternatively (fa) coupling the product obtained in step (d) or (e) with a compound of the general formula III

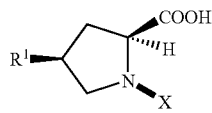

to wherein $R^1$ and X are as defined above;

(fb) removing the N-protecting group from the product thus obtained, and (fc) coupling the product thus obtained with an appropriately N-protected derivative of D-proline;

(g) removing the N-protecting group from the product obtained in step (f) or (fc);

(h) coupling the product thus obtained with an appropriately N-protected derivative of that amino acid which in the desired end-product is in position n, any functional group which may be present in said N-protected amino acid derivative being likewise appropriately protected;

(i) removing the N-protecting group from the product thus obtained;

(j) coupling the product thus obtained with an appropriately N-protected derivative of that amino acid which in the desired end-product is one position farther away from position n, any functional group which may be present in said N-protected amino acid derivative being likewise appropriately protected;

(k) removing the N-protecting group from the product thus obtained;

(l) repeating, if necessary, steps (j) and (k) until all amino acid residues have been introduced;

(m) detaching the product thus obtained from the solid support;

(n) cyclising the product cleaved from the solid support;

(o) removing any protecting groups present on functional groups of any members of the chain of amino acid residues and, if desired, any protecting group(s) which may in addition be present in the molecule; and (p) if desired, converting the product thus obtained into a salt or converting a salt thus obtained into the corresponding free compound of formula I or into a different salt.

DETAILED DESCRIPTION

Figure 1:
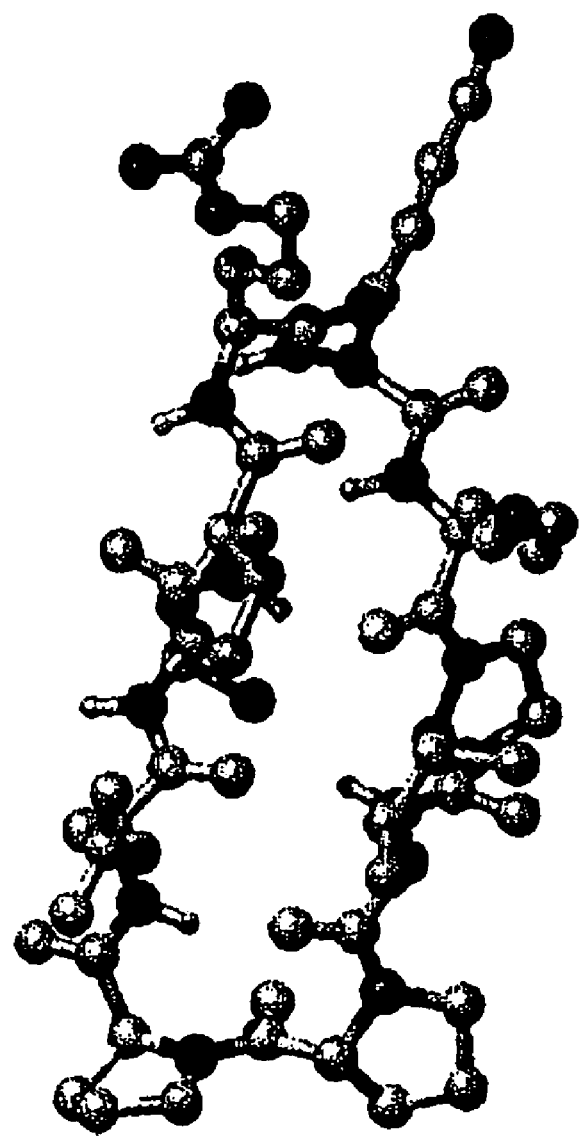
FIG. 1. Solution conformation of Example-1. The D-pro-L-Pro template is at the bottom. N-atoms are in black, other atoms in gray.

The process of the invention can advantageously be carried out as parallel array synthesis to yield libraries of template-fixed β-hairpin loop mimetics of the above general formula I. Such parallel synthesis allows one to obtain arrays of numerous (normally 24 to 192, typically 96) cyclic template-fixed peptides of general formula I in high yields and defined purities, minimizing the formation of dimeric and polymeric by-products. The proper choice of the functionalized solid-support (i.e. solid support plus linker molecule), templates and site of cyclization play thereby key roles.

The β-hairpin loop mimetics of formula I can mimick flat surfaces of proteins and thus be used to probe large surface protein-protein interactions. They can serve as lead finding tools for protein targets where it is notoriously difficult to find small-molecular-weight lead compounds. Due to the structurally and conformationally well-defined architecture of the β-hairpin loop mimetics of general formula I, key amino acid residues or motifs can be integrated in conformationally locked arrangements. By shifting these key amino acid residues or motifs along the β-hairpin structure various conformations can be scanned (conformational scanning of key sequences). Alternatively, protein sequences can be mapped in order to detect β-hairpin loop motifs.

This technique in summary allows to determine rapidly key amino acids and motifs (hotspots) important for binding in large surface and flat protein interfaces not only in their sequential but also in their spatial arrangement. This information can ultimately be used for the design of small peptidomimetic drug candidates (Cunningham, B. C.; Wells, J. A. *Curr. Opin. Struct. Biol.* 1997, 7, 457; Obrecht, D.; Altorfer, M.; Robinson, J. A. *Adv. Med. Chem.* Vol. 4, 1–68, JAI Press Inc., 1999).

Due to the enormous advances in genomic sciences increasing numbers of biologically relevant proteins (e.g. receptors, enzymes, transcription factors, ligands, modulators, chaperones) are becoming available in pure form for structural and functional studies. This burst of novel biological targets has also created a need for sources of new organic molecules for pharmaceutical and agrochemical screening and also for more efficient screening technologies. Combinatorial and parallel chemistry have emerged in recent years to satisfy the increasing demand for new families of novel compounds (Obrecht, D.; Villalgordo, J.-M, "Solid-Supported Combinatorial and Parallel Synthesis of Small-Molecular-Weight Compound Libraries", *Tetrahedron Organic Chemistry Series, Vol.* 17, Pergamon, Elsevier Science, 1998).

While general screening of small-molecular-weight compounds (MG<550) has successfully generated lead compounds for targets such as enzymes and receptors with well-defined binding sites and clefts, this technology gives rather poor results when ligand binding involves large surface protein-protein interactions with the corresponding receptors. These targets, however, are of increasing biological and pharmaceutical importance and many X-ray structures of such ligands, receptors and even ligands bound to their corresponding receptors are available. These include e.g. members of the growth factor family such as platelet-derived growth factor (PDGF) [Oefner, C; D'Arci, A.; Winkler, F. K.; Eggimann, B.; Hosang, M. *EMBO J.* 1992, 11, 3921], nerve growth factor (NGF) [Ibanez, C. F.; Ebendahl T.; Barbany, G.; Murray-Rust, J.; Blundell, T.; Perrson, H. *Cell,* 1992, 69, 320–341], epidermal growth factor (EGF) [*Biochemistry* 1992, 31, 236], basic fibroblast growth factor (b-FGF) [*Biochemistry* 1996, 35, 2086], transforming growth factor βII (TGF βII) [Schlunegger & Grütter, *J. Mol. Biol.* 1993, 231, 445], vascular endothelial growth factor (VEGF) [Müller et al., *Proc. Natl. Acad. Sci.* 1997, 94, 7192], and members of the cytokine family such as the interleukines, tumor necrosis factor (TNFα and β) [Banner, D. W.; D'Arci, A; Janes, W.; Gentz, R.; Schönfeld, H. J.; Broger, C.; Lötscher. H.; Lesslauer, W. *Cell,* 1993, 73, 431–445]. Moreover, chemokines [Tarby, C. M.; Saunders, J. *Drug Discovery Today* 1999, 4, 80–92; Ponath, P. D. *Exp. Opin. Invest. Drugs* 1998, 7, 1–16) including members of the CC-family such as RANTES, MCP-1-4, Eotaxin and others, and the CXC-family such as GROα-γ, interleukine 8 (II 8) and others have emerged as key mediators in a number of inflammatory pathologies. In addition, integrines [see Obrecht, D.; Altorfer, M.; Robinson, J. A. *Adv. Med. Chem.* Vol. 4, 1–68, JAI Press Inc., 1999] play key roles in cell adhesion, migration and proliferation. All these protein ligands bind to their corresponding receptors involving one or several large surface interactions. Moreover, X-ray crystallography and site directed mutagenesis studies highlight the importance of surface β-hairpin loop motifs to be key in those interactions.

The anatomy of large surface protein interfaces has recently been analysed and the average contact surface was determined to be typically 600–900 $Å^2$. The free energy of binding is not evenly distributed across the interfaces; instead, there are hot spots of binding energy made up of a small subset of residues in the dimer interface. These hot spots are enriched in tryptophan (Trp), tyrosine (Tyr) and arginine (Arg), and are surrounded by energetically less important residues that are most likely serving to occlude solvent from the hot spot [Bogan. A. A.; Thorn, K. S. *J. Mol. Biol.* 1998, 280, 1–9]. Occlusion of solvent is believed to be a necessary condition for highly energetic interactions. The β-hairpin loop motif offering two opposite β-sheet surfaces (e.g. a hydrophobic and a hydrophilic face) for possible binding interactions is ideally suited to meet these criteria for surface interactions.

The β-hairpin motif is very abundant in nature and occurs on the surface of many protein ligands and in the hypervariable domains of antibodies. The β-hairpin motif consists of two antiparallel β-strands linked by a short loop or turn and have been classified depending on the H-bonding network [Sibanda, B. L.; Blundell, T. L.; Thornton, J. M. *J. Mol. Biol.* 1989, 206, 759–777]. One example, par excellence, is found in the antigen binding sites of antibodies [Padlan, E. A, Mol. Immunol. 1994, 31, 169–217], which are composed of amino acid residues located in six so-called hypervariable loops or complementarity-determining-regions (CDR's), three each from the heavy- and light-chain variable regions ($v_H$ and $v_L$). Of the six CDR loops in antibodies of the Ig family, four may be classified as β-hairpins connecting adjacent antiparallel β-sheets, two from the $v_L$ domain, $L_2$ and $L_3$, and two from the $v_H$ domain, $H_2$ and $H_3$. Recent estimates suggest that a large majority of $L_1$, $L_2$, $L_3$, $H_1$ and $H_2$ hypervariable regions may be classified into one of 18 different canonical conformations [Chothia, C.; Lesk, A.; Gherardi, E.; Tomlinson, I. M.; Walter, G.; Marks, J. G.; Llewelyn, M. B.; Winter, G. *J. Mol. Biol.* 1992, 227, 799–817; Martin, A. C.; Thornton, J. M. J. Mol. Biol. 1996, 263, 800–815; Al-Lazikani, B.; Lesk, A.; Chothia, C. J. Mol. Biol. 1997, 273, 927–948].

The present invention provides a reliable process for the synthesis of template-fixed cyclic peptides of general formula I which mimick the various naturally occurring β-hairpin conformations, especially those present in growth factors, cytokines and chemokines, integrines and antibodies (see e.g. Figure, Example 1). Template structures corresponding to above formulae (a) through (h) have been shown to stabilize the H-bond network present in β-hairpins [e.g. for (a): Spaeth et al. *Helv. Chim. Acta* 1998, 81, 1726; Favre, M.; Moehle, K.; Jiang, L.; Pfeiffer, B.; Robinson, J. A. *J. Am. Chem. Soc.* 1999, 121, 2679–2685; for (b): Emery et al., *J. Chem. Soc. Chem. Comm.* 1996, 2155; Bisang et al. *J. Am. Chem. Soc.* 1998, 120, 7439; for (c): Pfeifer, M. *J. Chem. Soc. Chem. Commun.* 1998, 1977; for (d): Pfeifer et al. *Helv. Chim. Acta* 1997, 80, 1513; for (e): Beeli et al. *Helv. Chim. Acta* 1996, 79, 2235; and for (f) and analogues: Müller K.; Obrecht, D.; Knierzinger, A; Stankovic, C; Spiegler, C.; Trzeciak, A.; Englert, G.; Labhardt, A. M.; Schönholzer, P. *Perspectives in Medicinal Chemistry*; Testa, B., Kyburz, E., Fuhrer, W., Gyger, R., Eds.; Verlag Helv.

Chim. Acta: Basel, 1993; pp 513–531); for (g) and (h) and analogues: Müller, K.; Obrecht, D.; Knierzinger, A.; Spiegler, C.; Bannwarth, W.; Trzeciak, A; Englert, G.; Labhardt, A., Schönholzer, P. *Perspectives in Medicinal Chemistry*, Editor Testa, B.; Kyburz, E.; Fuhrer, W.; Giger, R L, Weinheim, New York, BaseL Cambridge: Verlag Helvetica Chimica Acta, 1993, 513–531; Bannwarth, W.; Gerber, F.; Grieder, A.; Knierzinger, A.; Müller, K.; Obrecht D.; Trzeciak, A. *Can. Pat. Appl.* CA2101599].

As stated above, the process of the invention takes advantage of a mixed solid- and solution phase synthetic approach which can be performed in a parallel array of e.g. 24–192, preferably 96, reactions, and provides the template-fixed cyclic peptides of general formula I in good yields and defined purities, ready for screening, thereby minimizing the amount of dimeric and polymeric impurities, which tend to give false positive hits in the screening process. This process is clearly superior to previously described syntheses of cyclic peptides by Bannwarth, W.; Gerber, F.; Grieder, A.; Knierzinger, A.; Müller, K.; Obrecht D.; Trzeciak, A. *Can. Pat. Appl.* CA2101599. The proper choice of resin and loading capacity, linker molecule, template and site of cyclization are key for obtaining high yields and reliable purities of β-hairpin loop mimetics. The templates thereby do not only stabilise the conformations of the final products, but they significantly enhance the rate of cyclization to the monomer, most probably by β-hairpin type H-bond induction.

Due to the well-defined architecture of the various β-hairpin loop mimetics of general formula I key amino acid residues and motifs can be locked in various conformations by shifting the sequence along the β-hairpin backbone ("conformational scanning of biologically active sequences"). Alternatively, protein sequences can be mapped by using this approach in order to detect β-hairpin conformations. Thus, this β-hairpin mimetics approach provides a technique to detect hot spots of high energy interactions in protein interfaces in three-dimensional arrangement. This information should ultimately be transferable into the design of small peptidomimetic molecules.

As used in the present description, the term "lower alkyl", taken alone or in combinations such as "aryl-lower alkyl", embraces straight chain or branched saturated hydrocarbon residues with up to 7, preferably up to 4 carbon atoms such as methyl ethyl n-propyl isopropyl, n-butyl, isobutyl, sec.-butyl, tert.-butyl and the like. The term "lower alkoxy" embraces alkyloxy groups in the sense of the above description of the term "lower alkyl", such as methoxy, ethoxy, n-butoxy, and the like. The term "aryl" embraces the phenyl residue and substituted phenyl residues, especially mono- or disubstituted phenyl residues, with lower alkyl or lower alkoxy groups or halogen atoms primarily coming into consideration as substituents. The term "halogen" denotes the four forms fluorine, chlorine, bromine and iodine unless indicated otherwise. The term "acyl" embraces residues of aliphatic and aromatic carboxylic acids, primarily on the one hand lower alkanoyl groups such as acetyl propionyl butyryl and the like, which can be substituted, for example by carboxy or lower alkoxycarbonyl, as is the case e.g. in 4-carboxybutyryl, 4-methoxycarbonylbutyryl or the like, and on the other hand aroyl groups such as the benzoyl group and substituted benzoyl groups, especially mono- or disubstituted benzoyl groups, with lower alkyl or alkoxy groups or halogen atoms primarily coming into consideration as substituents. The term "substituted lower alkyl" embraces lower alkyl groups which are substituted by protected amino, lower alkoxy, COOR$^{10}$ (in which R$^{10}$ is as above), carboxamido or N-lower alkylcarboxamido such as phthalimidomethyl, methoxymethyl, methoxyethyl and the like. The term "protected amino" embraces on the one hand residues such as phthalimido ("Pt") and the like and on the other hand residues of the formula —NH—R$^{11}$ in which R$^{11}$ can signify any appropriate N-protecting group such as benzyloxycarbonyl ("Z"), tert-butyloxycarbonyl ("Boc"), 9-fluorenylmethoxycarbonyl ("Fmoc"), allyloxycarbonyl ("Alloc"), trimethylsilylethoxycarbonyl ("Teoc"), trichloroethoxycarbonyl ("Tcc"), o-nitrophenylsulfonyl ("Nps") and the like.

As amino acid residues there primarily come into consideration those which are derived from natural α-amino acids. Hereinafter there is given a list of such amino acids which, or the residues of which, are suitable for the purposes of the present invention, the abbreviations corresponding to generally adopted usual practice.

| Ala | A | L-Alanine |
|---|---|---|
| Arg | R | L-Arginine |
| Asn | N | L-Asparagine |
| Asp | D | L-Aspartic acid |
| Cys | C | L-Cysteine |
| Glu | E | L-Glutamic acid |
| Gln | Q | L-Glutamine |
| Gly | G | Glycine |
| His | H | L-Histidine |
| Ile | I | L-Isoleucine |
| Leu | L | L-Leucine |
| Lys | K | L-Lysine |
| Met | M | L-Methionine |
| Phe | F | L-Phenylalanine |
| Pro | P | L-Proline |
| Ser | S | L-Serine |
| Thr | T | L-Threonine |
| Trp | W | L-Tryptophan |
| Tyr | Y | L-Tyrosine |
| Val | V | L-Valine |

Other α-amino acids which, or the residues of which, are suitable for the purposes of the present invention include

| $C_4$al | L-3-Cyclobutylalanine |
|---|---|
| $C_5$al | L-3-Cyclopentylalanine |
| $C_6$al | L-3-Cyclohexylalanine |
| aIle | L-Alloisoleucine |
| Nal | L-3-(1-Naphthylalanine) |
| Nle | L-Norleucine |
| Nva | L-Norvaline |
| Orn | L-Ornithine |
| Orn(CHO) | $N^5$-Formyl-L-ornithine |
| L-Phg | L-Phenylglycine |
| Tza | L-3-(2-Thiazolyl)alanine |

It will be appreciated that the compound of the above general formula III, i.e. one of the two building blocks of the template structure corresponding to the above formula (a), is a derivative of L-proline (L-Pro, $^L$P), whilst the second of these building blocks is a residue of D-proline (D-Pro, $^D$P).

Preferred values for n, i.e. the number of amino acid residues present in the chain Z, are, in general, 4–16. Particularly preferred values of n are 6, 10 and 14 in case the template structure corresponds to the above formula (b) or (c) or (d), and 4, 5, 6, 8, 12 and 16 in the case of the other template structures, i.e. those corresponding to the above formulae (a), (e), (t), (g) and (h).

Advantageously the chain Z consist of, or contains, a key sequence of two, three, four, five, six or occasionally up to ten amino acid residues, the two terminal members of which are "constant" ("k") whilst any other members are either "constant", too or "variable" ("x"), in all possible combinations or permutations. The two terminal "constant" members can be the same or different, and the same applies to any remaining "constant" and/or to any "variable" members.

Particularly suitable "constant" members ("k") are Trp, Arg, Tyr, Ile, As, His, Lys, Glu and Thr, further suitable "constant" members ("k") are Gln, Phe, Met and Ser, and suitable "variable" members ("x") are Ala, Orn, Leu and Val.

Key sequences of two, three, four, five and six amino acid residues, can be schematically depicted as follows:

dipeptide
-$k^1$-$k^2$-
tripeptide
-$k^1$-$k^2$-$k^3$-
-$k^1$-$x^1$-$k^2$-
tetrapeptide
-$k^1$-$k^2$-$k^3$-$k^4$-
-$k^1$-$x^1$-$k^2$-$k^3$-
-$k^1$-$k^2$-$x^1$-$k^3$-
-$k^1$-$x^1$-$x^2$-$k^2$-
pentapeptide
-$k^1$-$k^2$-$k^3$-$k^4$-$k^5$-
-$k^1$-$x^1$-$k^2$-$k^3$-$k^4$-
-$k^1$-$k^2$-$x^1$-$k^3$-$k^4$-
-$k^1$-$k^2$-$k^3$-$x^1$-$k^4$-
-$k^1$-$x^1$-$k^2$-$x^2$-$k^3$-
-$k^1$-$k^2$-$x^1$-$x^2$-$k^3$-
-$k^1$-$x^1$-$k^2$-$x^2$-$k^3$-
-$k^1$-$x^1$-$x^2$-$x^3$-$k^2$-
hexapeptide
-$k^1$-$k^2$-$k^3$-$k^4$-$k^5$-$k^6$-
-$k^1$-$x^1$-$k^2$-$k^3$-$k^4$-$k^5$-
-$k^1$-$k^2$-$x^1$-$k^3$-$k^4$-$k^5$-
-$k^1$-$k^2$-$k^3$-$x^1$-$k^4$-$k^5$-
-$k^1$-$k^2$-$k^3$-$k^4$-$x^1$-$k^5$-
-$k^1$-$x^1$-$x^2$-$k^2$-$k^3$-$k^4$-
-$k^1$-$k^2$-$x^1$-$x^2$-$k^3$-$k^4$-
-$k^1$-$k^2$-$k^3$-$x^1$-$x^2$-$k^4$-
-$k^1$-$x^1$-$k^2$-$x^2$-$k^3$-$k^4$-
-$k^1$-$x^1$-$k^2$-$k^3$-$x^2$-$k^4$-
-$k^1$-$k^2$-$x^1$-$k^3$-$x^2$-$k^4$-
-$k^1$-$x^1$-$k^2$-$x^2$-$x^3$-$k^3$-
-$k^1$-$k^2$-$x^1$-$x^2$-$x^3$-$k^3$-
-$k^1$-$x^1$-$x^2$-$k^2$-$x^3$-$k^3$-
-$k^1$-$x^1$-$x^2$-$x^3$-$k^2$-$k^3$-
-$k^1$-$x^1$-$x^2$-$x^3$-$x^4$-$k^2$-

Certain key sequences are known to occur in important physiologically active peptides, such as

| | |
|---|---|
| R G D | in fibronectin (FN), vitronectin (VN), osteopontin, collagens, thrombospondin, fibrinogen (Fg), von Willebrand factor (vWF), see Obrecht, D.; Altorfer, M.; Robinson, J. A. Adv. Med. Chem. Vol. 4, 1–68, JAI Press Inc., 1999 |
| E L R | in C X C chemokines, see Saunders, J.; Tarby, C. M. Drug Discovery Today, 1999, 4, 80–92 |
| R K K | see J. Biol. Chem. 1999, 274, 3513 |
| K G F | see Prot. Sci. 1998, 7, 1681–1690 |
| V R K K | [SEQ ID NO: 1] in Platelet-Derived Growth Factor (PDGF), see Ross, R.; Raines, E. W.; Bowden-Pope, D. F. Cell, 1986, 46, 155–159 |
| K K Y L | [SEQ ID NO: 2] in VIP (vasointestinal peptide) showing neuroprotective properties against β-amyloid neurotoxicity, see Proc. Natl. Am. Soc. USA 1999, 96, 4143–4148 |
| W L D V | [SEQ ID NO: 3] in integrin $\alpha_4\beta_1$, see Europ. J. Biol. 1996, 242, 352–362 and Int. J. Pept. Prot. Res. 1996, 47, 427–436 |
| Y I R L P | [SEQ ID NO: 4] in Factor Xa inhibitors, see Al Obeidis, F.; Ostrem, J. A. Drug Discovery Today 1998, 3, 223–231 |
| Y I G S R | [SEQ ID NO: 5] in laminine, see EMBO. J. 1984, 3, 1463 |
| I K V A V | [SEQ ID NO: 6] see Cell 1987, 88, 989 |
| P P R X X W | [SEQ ID NO: 7] see J. Biol. Chem. 1998, 273, 11001–11006 & 11007–11011 |
| I Y Y K D G A L K Y | [SEQ ID NO: 8] see Biochem Soc. Trans. 1997, 29, 387–392 |

If desired, the process of the invention can be modified to give the enantiomers of the compounds of the general formula I. To this effect all amino acids which have an asymmetric α-carbon atom are used in their D-Form and the enantiomer of a template corresponding to structure (a), (b), (c), (d) or (e) or a template corresponding to formula (f), (g) or (h) is used in step (f) and, respectively, the enantiomer of a compound of formula III is used in step (fa) and a derivative of L-proline is used in step (fc).

Suitable protecting groups for amino acids and, respectively, for their residues are, for example, for the amino group (as is present e.g. also in the side-chain of lysine)

| | |
|---|---|
| Z | benzyloxycarbonyl |
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Tr | triphenymethyl or trityl | for the carboxyl group (as is present e.g. also in the side-chain of aspartic and glutamic acid) by conversion into esters with the alcohol components

| | |
|---|---|
| tBu | tert.-butyl |
| Bn | benzyl |
| Me | methyl |
| Ph | phenyl |
| Pac | Phenacyl |
| | Allyl |

-continued

| | |
|---|---|
| | trimethylsilylethyl |
| | trichloroethyl; | for the guanidino group as is present e.g. in the side-chain of arginine)

| | |
|---|---|
| Pmc | 2,2,5,7,8-pentamethylchroman-6-sulfonyl |
| Ts | tosyl (i.e. p-toluenesulfonyl) |
| Z | benzyloxycarbonyl |
| Pbf | pentamethyldihydrobenzofuran-5-sulfonyl | for the hydroxy group (as is present e.g. in the side-chain of threonine and serine)

| | |
|---|---|
| tBu | tert.-butyl |
| Bn | benzyl |
| Tr | trityl | and for the mercapto group (as is present e.g. in the side-chain of cysteine)

| | |
|---|---|
| tBu | tert.-butyl |
| Bn | benzyl |
| Tr | trityl |
| Mtr | 2-methoxytrityl. |

The functionalize solid support is conveniently derived from polystyrene crosslinked with, preferably 1–5%, divinylbenzene; polystyrene coated with polyethyleneglycol spacers (Tentagel$^R$); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention the linker must be designed to eventually release the carboxyl group under mild acidic conditions which do not affect protecting groups present on any functional group in the side-chains of the various amino acids. Linkers which are suitable for the purposes of the present invention form acid-labile esters with the carboxyl group of the amino acids, usually acid-labile benzyl, benzhydryl and trityl esters; examples of linker structures of this kind include 3-methoxy-4-hydroxymethylphenoxy (Sasrin linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl.

When carried out as a parallel array synthesis the process of the invention can be advantageously carried out as described hereinbelow but it will be immediately apparent to those skilled in the art how this procedure will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support, preferably 1 to 3% cross linked polystyrene or tentagel resin.

The solvent to be used must be capable of swelling the resin and includes, but is not limited to, dichloromethane (DCM), dimethylformamide (DMF), N-methylpyrrolidinone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202–4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin$^R$ linker, Mergler et al., *Tetrahedron Lett.* 1988, 29 4005–4008) is cleavable with diluted trifluoroacetic acid (0.5–1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2, 4-dimethoxyphenyl-hydroxymethyl)phenoxy linker (Rink linker, Rink, H. *Tetrahedron Lett.* 1987, 28, 3787–3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943–3946), which allows the peptide detachment using a mixture of glacial acetic acid/trifluoroethanol/DCM (1:2: 7) for 30 min.

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used if required to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067–1068) or diisopropylcarbodiimide (DIC, Sarantakis et al *Biochem. Biophys. Res. Commun.* 1976, 73, 336–342), the resulting dicyclohexylurea is insoluble and, respectively, diisopropylurea is soluble in the solvents generally used. In a variation of the carbodiimide method 1-hydroxybenzotriazole (HOBt, König & Geiger, *Chem. Ber* 1970, 103, 788–798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazole-1-yl-oxy-tris-(dimethylamino)phosphonium hexafluorophosphate (BOP) (Castro et al., *Tetrahedron Lett.* 1975, 14, 1219–1222; *Synthesis,* 1976, 751–752), or benzotriazole-1-yl-oxy-tris-pyrrolidino-phosphonium hexaflurophoshate (Py-BOP, Coste et al., *Tetrahedron Lett.* 1990, 31, 205–208), or 2-(1H-benzotriazole-1-yl-)1,1,3,3-tetramethyluronium terafluoroborate (TBTU), or hexaflurorophosphate (HBTU, Knorr et al., *Tetrahedron Lett.* 1989, 30, 1927–1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279–2281) have also been used as coupling reagents.

Due to the fact that near-quantitative coupling reactions are essential it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can be easily and quickly performed after each coupling step. Fmoc chemistry allows the spectrophotometric detection of the Fmoc chromophore when it is released with the base (Meienhofer et al., *Int. J. Peptide Protein Res.* 1979, 13, 3542).

The resin-bound intermediate within each reaction tube is washed clean of excess of retained reagents, of solvents, and of by-products by repetitive exposure to clean solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;

2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and byproduct removal by methods such as TLC, GC, or visualization of the wash filtrates.

The above described procedure of reacting the resin-bound compound with reagents within the reaction wells followed by removal of excess reagents, by-products, and solvents is repeated with each successive transformation until the final resin-bound compound is prepared.

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated, then cyclization is effected in solution using solvents such as DCM, DMF, Dioxane, THF and the like. Various coupling reagents which were mentioned earlier can be used for the cyclization. The duration of the cyclization is about 6–48 hours, preferably about 24 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

The fully protected cyclized peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably 2 hours. Thereafter most of the TFA is evaporated and the product is precipitated with ether/hexane (1:1) or other solvents which are suitable therefor. After careful removal of the solvent, the cyclic peptide derivative obtained as end-product can be isolated. Depending on its purity, this peptide derivative can be used directly for biological assays, or it has to be further purified, for example by preparative HPLC.

The end-products, i.e. the compounds of formula I, can be individually tested for biological activity once they have been isolated and characterized. For example, the following Solid-Phase assay can be carried out.

Direct immobilization of platelet-derived growth factor β (PDGFR-β) is performed by overnight incubation in immunosorbent 96-well plates (Nunc) at 4° C. using 100 ng of purified protein in 100 μl of 15 mM $Na_2CO_3$, 35 mM $NaHCO_3$, pH 9.6. The plates are washed once with tris-buffered saline (TBS, 20 mM Tris-HCl, 150 mM NaCl pH 7.4), and nonspecific adsorption is blocked by at least 1 h of incubation with TBS plus 1% bovine serum albumin (BSA).

Following washing with TBS plus 0.1% Tween, 3000 cpm of $^{125}$I-PDGF-BB and increasing amounts of unlabeled PDGF-BB or the peptide derivative of formula I are added to duplicate wells and incubated for 3 h at room temperature in 0.1% Tween, 1 mM $CaCl_2$, 1 mM $MgCl_2$ and 1% BSA. The plates are washed three times with TBS plus 0.1% Tween, and bound ligand is removed with 0.1M citric acid, pH 2.5, prior to counting in a γ-counter.

Some of the compounds embraced by general formula I have already been described but the remaining of these compounds are novel and form part of the present invention, namely those of formula I with the provisos that if

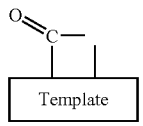

is
(i) group (a) and $R^1$ is hydrogen, then Z is other than

```
-Val-Lys-Asn-Tyr-Gly-Val-Lys-Asn-    [SEQ ID NO: 9]
Ser-Glu-Trp-Ile-,

-Val-Lys-Asn-Tyr-Gly-Val-Lys-Asn-    [SEQ ID NO: 10]
Ser-Glu-Trp-Thr-,

-Gly-Arg-Gly-Asp-,                    [SEQ ID NO: 11]

-Arg-Gly-Asp-Gly-,                    [SEQ ID NO: 12]

-Phe-Tyr-Thr-Gly-Thr-,                [SEQ ID NO: 13]

-Tyr-Arg-Asp-Ala-Met-,                [SEQ ID NO: 14]

-Asn-Thr-Tyr-Ser-Gly-Val-,            [SEQ ID NO: 15]

-Trp-Asp-Asp-Gly-Ser-Asp- and         [SEQ ID NO: 16]

-Leu-Trp-Tyr-Ser-Asn-His-Trp-Val-;    [SEQ ID NO: 17]
```

(ii) group (b) and $R^2$ is hydrogen or $CH_2COOH$, or group (c) and $R^3$ is benzoyl, or group (d), or group (e), then Z is other than -Ala-Asn-Pro-Asn-Ala-Ala- [SEQ ID NO:18];
(iii) group (b) and $R^2$ is hydrogen, then Z is other than -Ala-Arg-Gly-Asp- [SEQ ID NO:19];
(iv) group (f), $R^4$ is methyl, $R^5$ is methoxy and $R^6$ and $R^7$ each are hydrogen, then Z is other than

```
-Val-Ala-Ala-Phe-Leu-Ala-Leu-Ala-,    [SEQ ID NO: 20]

-Arg-Gly-Asp-Val-,                    [SEQ ID NO: 21]

-Ala-Thr-Val-Gly-,                    [SEQ ID NO: 22]

-Glu-Arg-Gly-Asp-Val-Tyr-,            [SEQ ID NO: 23]

-Ile-Ala-Arg-Gly-Asp-Phe-Pro-Asp-,    [SEQ ID NO: 24]

-Ala-Arg-Ile-Ala-Arg-Gly-Asp-Phe-     [SEQ ID NO: 25]
Pro-Asp-Asp-Arg-,

-Ala-Arg-Gly-Asp-Phe-Pro-,            [SEQ ID NO: 26]

-Arg-Gly-Asp-Phe- and                 [SEQ ID NO: 27]

-Arg-Ile-Ala-Arg-Gly-Asp-Phe-Pro-     [SEQ ID NO: 28]
Asp-Asp-;
```

(v) group (g), $R^8$ is methyl and $R^9$ is methyl or n-hexyl, or group (h), $R^8$ is ethyl and $R^9$ is ethyl, then Z is other than -Arg-Gly-Asp-Val- [SEQ ID NO:21];
(vi) group (g), $R^8$ is methyl and $R^9$ is methyl or benzyl, then Z is other than -Gly-Gly-Ala-Gly- [SEQ ID NO:29];
(vii) group (g), $R^8$ is methyl and $R^9$ is methyl, then Z is other than Gly-Asp-Gly-Gly- [SEQ ID NO:30]; and
(viii) group (g), $R^8$ is methyl and $R^9$ is n-hexyl, then Z is other than -Val-Arg-Lys-Lys- [SEQ ID NO:1].

The enantiomers of all compounds of formula I are novel and also form part of the present invention.

The compounds of formula II incorporating structures (a) to (h) and the compounds of formula III can be prepared as shown in the following Reaction Schemes. Throughout these Reaction Schemes the N-protecting group X present in the compounds of formulae II and III is indicated to be Fmoc, the preferred value for X, but it will be appreciated that corresponding compounds carrying as X other N-protecting groups can be prepared in a similar way.

Reaction Scheme 1

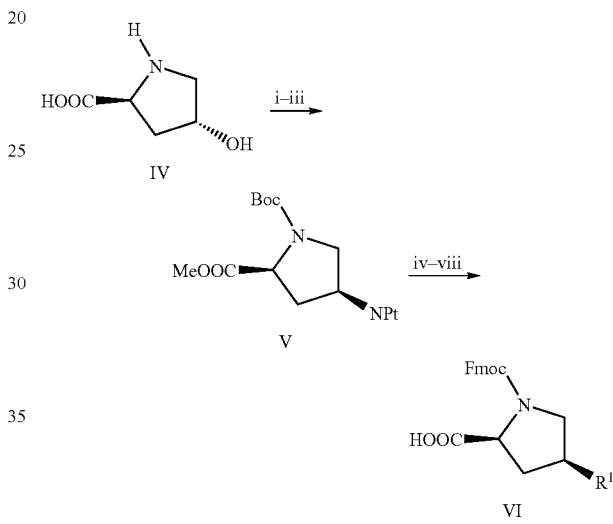

IV ⟶ V
i: Treatment of IV with a dehydrating reagent such as thionylchloride in methanol at an elevated temperature, conveniently at reflux.
ii: Introduction of Boc, e.g. using di-tert.-butyl dicarbonate and triethylamine in a suitable solvent such as dichloromethane; any other suitable N-protecting group (not shown in Reaction Scheme 1) can be introduced in an analogous manner.
iii: Reaction of formed product with phthalimide, diethyl diazodicarboxylate and triphenylphoshine under standard Mitsunobu conditions (Mitsunobu, O.; Wada, M.; Sano, T.J. *J. Am. Chem. Soc.* 1972, 94, 672) to conveniently yield V.

V ⟶ VI
iv: Cleavage of the phthalimide group, suitably by treatment of V with hydrazine hydrate in a suitable solvent, such as ethanol, at an elevated temperature, conveniently at about 80° C.
v: Standard protection of the 3-amino group.
vi: Saponification of the methyl ester group using e.g. a suitable basic reagent such as lithium hydroxide in methanol and water.
vii: The tert.-butoxycarbonyl group is subsequently cleaved off using reagents such as trifluoroacetic acid in dichloromethane or 4N hydrochloric acid in dioxane.
viii: The formed amino acid is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield VI.

Reaction Scheme 2

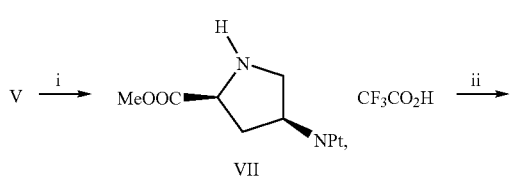

-continued

VIII

IX (structure with HOOC, NHFmoc, HN, O)

V → VII i: Treatment of V with trifluoracetic acid in dichloromethane.

VII → VIII ii: VII is coupled under standard peptide coupling conditions with Z-Asp(tBu)OH in DMF with reagents such as HBTU and 1-hydroxybenztriazole (HOBt) with a base such as diisopropylethylamine to yield VIII.

VIII → IX iii: Removal of the Z-group, conveniently by hydrogenation using $H_2$ and a catalyst such as Palladium on charcoal, in solvents such as ethanol, DMF and ethyl acetate.

iv: The phthalimide group is cleaved off from the resulting product, conveniently by treatment with hydrazine in a suitable solvent such as ethanol at an elevated temperature, suitably at about 80° C.

v: The formed amino acid is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield IX as described by Bisang, C.; Weber, C.: Robinson, J. A. Helv. Chim. Acta 1996, 79, 1825–1842.

Reaction Scheme 3

IV →(i–iii) X →(iv, v) XI →(vi, vii) XII →(viii, ix)

-continued

XIII

XIV

IV → X i: Treatment of IV with a dehydrating reagent such as thionyl chloride in a suitable solvent such as methanol at an elevated temperature, conveniently at reflux.

ii: The resulting amino acid ester is N-protected under standard conditions for introducing the Z group, e.g. using benzyloxycarbonyl chloride and triethylamine in a suitable solvent such as dichloromethane.

iii: The Z-protected amino acid methyl ester is treated with trimethylsilylchloride and a base such as triethylamine in a solvent such as tetrahydrofuran, cooled, conveniently to about -78° C., followed by reaction with a strong base such as lithium diisopropylamide or lithium hexamethyldisilylazide and tert.-butyl bromoacetate yielding X as a mixture of diastereomers as described by Bisang, C.; Jiang, L.; Freund, E.; Emery, F.; Bauch, C.; Matile, H.; Pluscke, G.; Robinson, J. A. J. Am. Chem. Soc. 1998, 120, 7439–7449; Emery, F.; Bisang, C.; Favre, M.; Jiang, L.; J. Chem. Soc. Chem. Commun. 1996, 2155–2156.

X → XI iv: Reaction of X with phthalimide, diethyl diazadicarboxylate and triphenylphoshine under standard Mitsunobu conditions (Mitsunobu, O.; Wada, M.; Sano, T. J. J. Am. Chem. Soc. 1972, 94, 672.

v: The resulting product is hydrogenated using $H_2$ and a suitable catalyst such as Palladium on charcoal in a solvent such as ethyl acetate, DMF or ethanol; subsequently separation of diastereomers takes place.

XI → XII vi: XII is coupled with Fmoc-Asp(allyl)OH under standard peptide coupling conditions using reagents such as HATU, HOAt and a base such as diisopropylethylamine in a suitable solvent such as DMF.

vii: Cyclization, conveniently with DBU in DMF.

XII → XIII viii: The phthalimide group is cleaved off from resulting product, conveniently by hydrazinolysis, e.g. treatment with methylhydrazine in a suitable solvent such as DMF.

ix: The formed product is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane.

XIII → XIV x: Standard removal of an allyl ester group using e.g. Palladium(0) as catalyst.

Reaction Scheme 4

Vitamin C ⟹ XV →(i–viii)

-continued

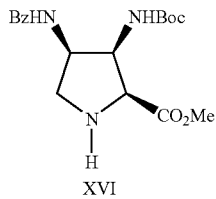
XVI

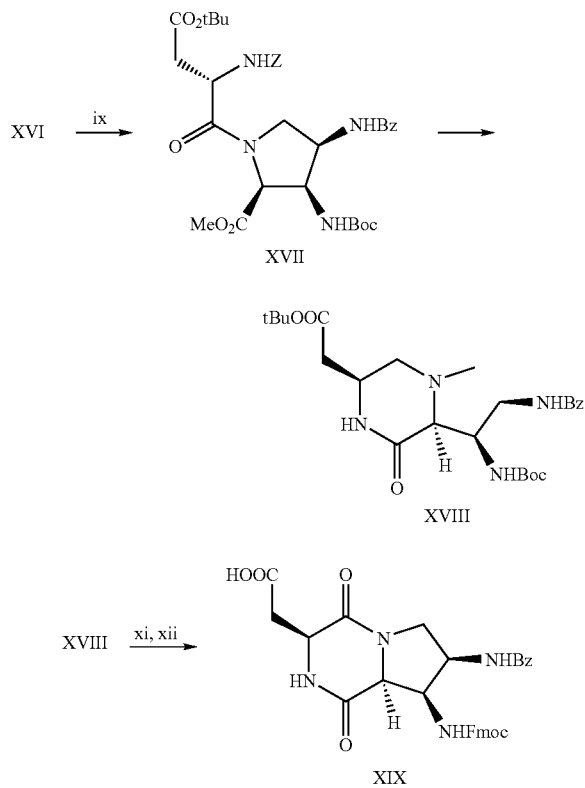
XVII

XVIII

XIX

XV ⟶ XVI
 i: XV (obtainable from Vitamin C as described by Hubschwerlen, C. (*Synthesis* 1986, 962) is treated with phthalimide, diethyl diazodicarboxylate and triphenylphoshine under standard Mitsunubo conditions (Mitsunubo, O.; Wada, M.; Sano, T. *J. Am. Chem. Soc.* 1972, 94, 672).
 ii: The phthalimide group is cleaved off from the product, conveniently by hydrazinolysis, e.g. by treatment with methylhydrazine in a suitable solvent such as DMF.
 iii: The amino group is protected by treatment with a benzoylating reagent such as benzoic acid anhydride or benzoylchloride and a base such as triethylamine or 4-dimethylaminopyridine in a suitable solvent such as dichloromethane or DMF.
 iv: Removal of the 2,4-dimethoxybenzyl group, e.g. with $K_2S_2O_8$ and $Na_2HPO_4$ in aqueous acetonitrile at an elevated temperature, e.g. at about 80° C.
 v: Introduction of a tert.-butoxycarbonyl group using e.g. di-tert.-butyloxycarbonyl dicarbonate, triethylamine and a catalytic amount of 4-dimethylaminopyridin in a suitable solvent such as dichloromethane.
 vi: Reaction with aqueous sodium carbonate in tetrahydrofuran followed by acidification.
 vii: Esterification of the carboxylic acid group, conveniently with diazomethane in a suitable solvent as diethylether.
 viii: Removal of the Z-group, conveniently by hydrogenation with $H_2$ in the presence of a catalyst such as Palladium on charcoal in a solvent such as DMF to yield XVI as described by Pfeifer, M.; Robinson, J. A. *J. Chem. Soc. Chem. Commun.* 1998, 1977.

XVI ⟶ XVII
 ix: XVI is coupled under standard peptide coupling conditions with Z-Asp(tBu)OH in DMF with reagents such as HBTU and 1-hydroxybenztriazole with a base such as diisopropylethylamine to yield XVII as described by Pfeifer, M.; Robinson, J. A. *J. Chem. Soc. Chem. Commun.* 1998, 1977.

XVII ⟶ XVIII
 x: Removal of the Z-group, e.g. by hydrogenation using $H_2$ and a catalyst such as Palladium on charcoal under standard conditions, yields XVIII as described by Pfeifer, M.; Robinson, J. A. *J. Chem. Soc. Chem. Commun.* 1998, 1977.

-continued

XVIII ⟶ XIX
 xi: Cleavage of the tert.-butyl ester and tert.-butyloxycarbonyl groups, conveniently using trifluoracetic acid in dichloromethane or 4N hydrochloric acid in dioxane.
 xii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield XIX as described by Pfeifer, M.; Robinson, J. A. *J. Chem. Soc. Chem Commun.* 1998, 1977.

Reaction Scheme 5

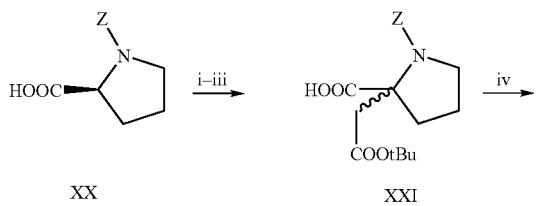
XX     XXI

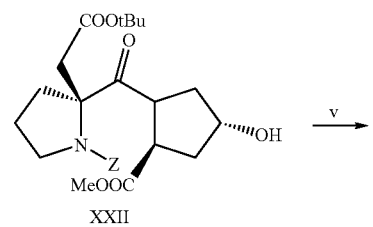
XXII

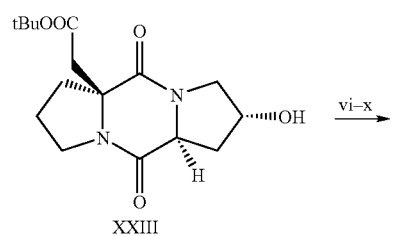
XXIII

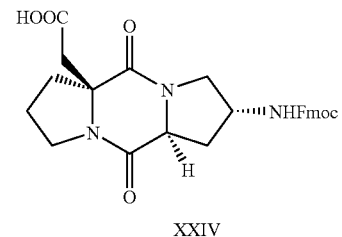
XXIV

XX ⟶ XXI
 i: Treatment of XX wit a dehydrating agent such as thionyl chloride in a suitable solvent such as methanol at an elevated temperature, conveniently at about 80° C.
 ii: The intermediate is treated with a strong base such as lithium diisopropylamide or lithium hexamethyldisilylazide in a suitable solvent such as tetrahydrofuran at low temperature, and with tert.-butyl bromoacetate as described by Pfeifer, M.; Linden, A.; Robinson, J. A. *Helv. Chim Acta* 1997, 80, 1513–1527.
 iii: Saponification using a base such as lithium hydroxide in water and a suitable solvent such as methanol.

XXI ⟶ XXII
 iv: Coupling of XXI with (2S,4R)-Z-hydroxy proline under standard peptide coupling conditions, e.g. using reagents such as HBTU and HOBT and diisopropylethylamine as base in a suitable solvent such as DMF, yielding XXII as described by Pfeifer, M.; Linden, A.; Robinson, J. A. *Helv. Chim. Acta* 1997, 80, 1513–1527.

XXII ⟶ XXIII
 v: Removal of the Z-group, e.g. by hydrogenation using $H_2$ and a catalyst such as Palladium on charcoal in a suitable solvent such as ethyl acetate.

-continued

XXIIII ⟶ XXIV vi: XXIII is converted into the corresponding tosylate according to standard methods, e.g. by reaction with p-toluenesulfonyl chloride in pyridine.
vii: The intermediate tosylate is converted into the corresponding azide, e.g. by treatment with sodium azide in a suitable solvent such as DMF at an elevated temperature, conveniently at about 80° C.
viii: Reduction of the azide group to the amino group can conveniently be performed with H$_2$ and a catalyst such as Palladium on charcoal in a suitable solvent such as ethyl acetate, or with triphenylphoshine.
ix: The intermediate free amino acid tert.-butylester is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane.
x: Acidolysis using e.g. trifluoroacetic acid in dichloromethane gives conveniently XXIV as described by Pfeifer, M.; Linden, A.; Robinson, J. A. *Helv. Chim. Acta* 1997, 80, 1513–1527.

Reaction Scheme 6

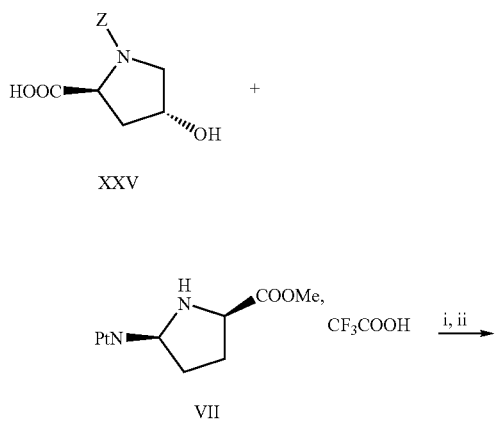

XXV ⟶ XXV i: Standard peptide coupling of VII with XXV under standard peptide coupling conditions using reagent such as HBTU and HOBT and e.g. diisopropylethylamine as base in a suitable solvent such as DMF.
ii: Hydrogenation using H$_2$ and a catalyst such as Palladium on charcoal in solvents such as ethyl acetate, DMF and ethanol yields XXVI as described by Beeli, R.; Steger, M.; Linden, A.; Robinson, J. A. *Helv. Chim. Acta* 1996, 79, 2235–2248.

XXVI ⟶ XXVII iii: Oxidation of the OH group using reagents such as pyridine-sulfur trioxide complex, Jones reagent or the Dess-Martin periodinane reagent.
iv: Wittig-Horner condensation of the intermediate ketone with (MeO)$_2$POCH$_2$COOMe and a base such as sodium hexamethyldisilylazide in solvents such as tetrahydrofuran or dimethoxy as described by Beeli, R.; Steger, M.; Linden, A.; Robinson, J. A. *Helv. Chim. Acta* 1996, 79, 2235–2248.
v: Stereoselective hydrogenation of the double bond using e.g. H$_2$ and a catalyst such as Palladium on charcoal in a solvent such as ethanol, DMF and ethyl acetate.
vi: Hydrazinolysis of the intermediate phthalimide using e.g. hydrazine in a suitable solvent such as ethanol at an elevated temperature, conveniently at about 80° C.
vii: Saponification of the methyl ester group, e.g. by treatment with a suitable basic reagent such as lithium hydroxide in water and methanol.
viii: The intermediate free amino acid formed is conveniently protected with reagents such as 9-fluorenylmethoxcarbonyl chloride or 9-fluorenylmethoxcarbonyl succinimde using a base such as sodium carbonate or triethylamine in a suitable solvent or mixture of solvents such as dioxane and water, or dichloromethane to yield XXVII as described by Beeli, R.; Steger, M.; Linden, A.; Robinson, J. A. *Helv. Chim. Acta* 1996, 79, 2235–2248.

Reaction Scheme 7

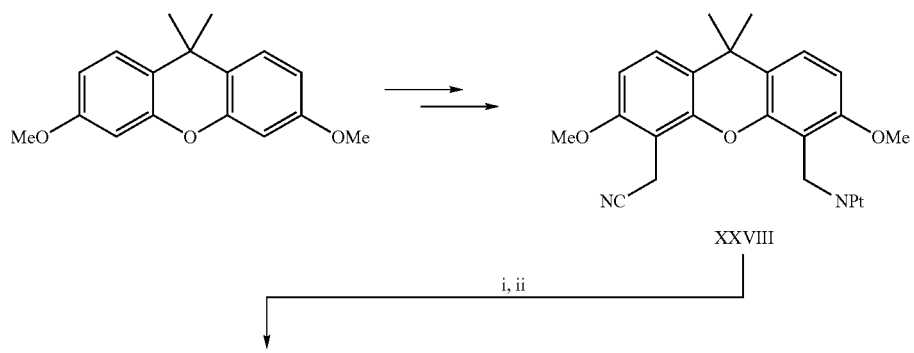

-continued

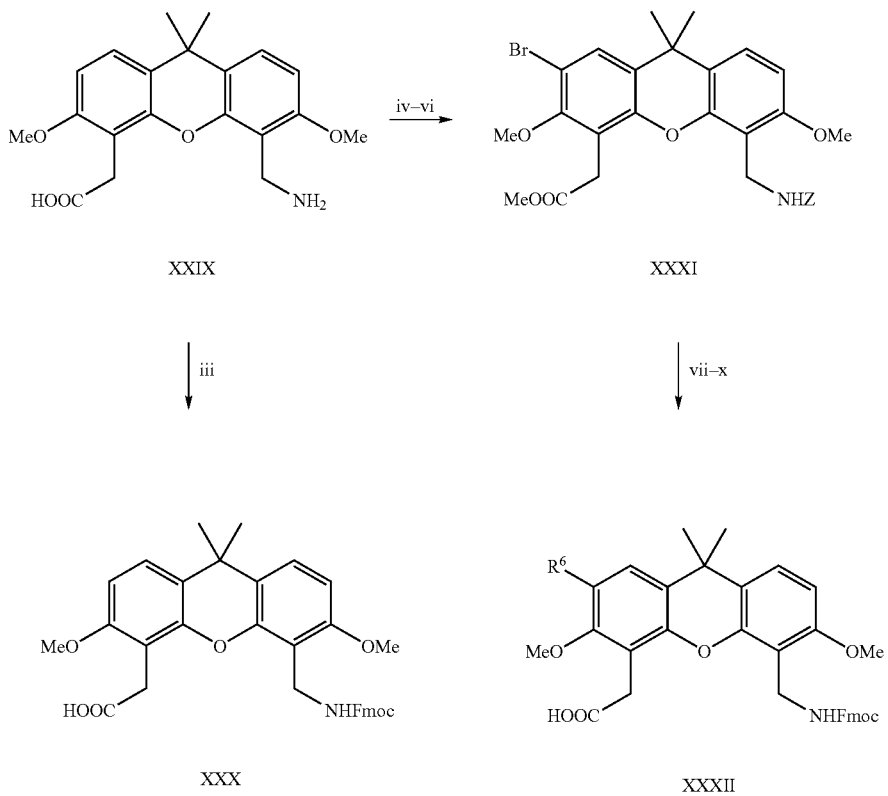

XXXVIII ⟶ XXIX i: XXVIII can be synthesized according to P. Waldmeier, "Solid-supported synthesis of highly substituted xanthene-derived templates for the synthesis of B-turn stabilized cyclic peptide libraries", PhD-thesis, University of Zurich, 1996. For cleaving the phthalimide group XXVIII is conveniently submitted to hydrazinolysis e.g. by treatment with hydrazine hydrate in a suitable solvent such as ethanol at an elevated temperature e.g. at about 80° C.

ii: The intermediate aminonitrile is saponified, conveniently under basic conditions, e.g. with aqueous sodium hydroxide in a suitable solvent such as ethanol at an elevated temperature, conveniently under reflux, to yield XXIX.

XXIX ⟶ XXX iii: The intermediate free amino acid formed is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield XXX as described by P. Waldmeier, "Solid-supported synthesis of highly substituted xanthene-derived templates for the synthesis of B-turn stabilized cyclic peptide libraries", PhD-thesis, University of Zurich, 1996.

XXIX ⟶ XXXI iv: Regioselective bromination of XXOX is performed preferably with bromine in acetic acid and dichloromethane. In a similar fashion $R^6$ = $NO_2$ can be introduced by treatment with $HNO_3$ in acetic acid and $R^6$ = $CH_2$-NPt by treatment with hydroxymethyl phthalimide in $H_2SO_4$.

v: The amino group is conveniently Z-protected with reagents such as benzyloxycarbonyl chloride or succinimide in a suitable solvent such as dioxane in presence of a base such as aqueous sodium hydroxide.

vi: The carboxylic acid group is esterified, preferably with DBU and methyl iodide in DMF.

XXXI ⟶ XXXII vii: Introduction of lower alkyl, substituted lower alkyl and aryl substituents ($R^6$), conveniently by Palladium(0)- catalyzed Stille- (Stille, J.K. *Angew. Chem.* 1986, 68, 504) and Suzuki-couplings (Oh-e, T.; Mijaura, N.; Suzuki, A. *J. Org. Chem.* 1993, 58, 2201).

viii: Removal of the Z-group, e.g. by hydrogenation using $H_2$ and a catalyst such as Palladium on charcoal in a suitable solvent such as ethanol, DMF and ethyl acetate.

ix: Hydrolysis of the ester group, conveniently under acidic conditions, e.g. with 25% aqueous hydrochloric acid in a suitable solvent such as dioxane at an elevated temperature, preferably at about 100° C.

x: The intermediate free amino acid formed is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield XXXII.

Reaction Scheme 8

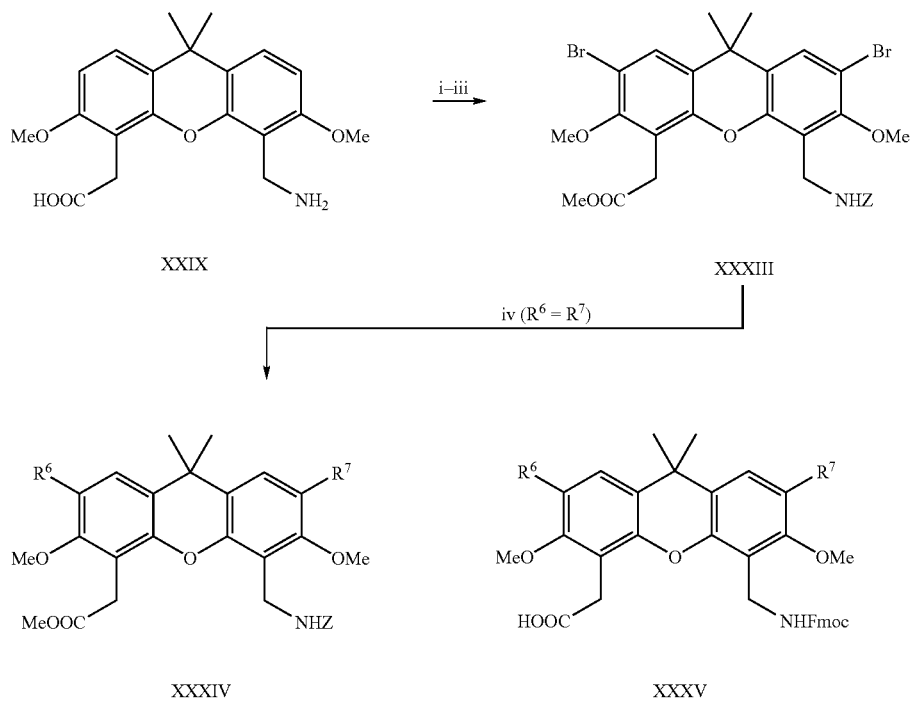

XXIX → XXXIII
- i: Double ortho- bromination is performed preferably with excess bromine in acetic acid and dichloromethane. In a similar fashion $R^6 = R^7 = NO_2$ can be introduced by treatment with $HNO_3$ in acetic acid and $R^6 = R^7 = CH_2\text{-NPt}$ by treatment with hydroxymethyl phthalimide in $H_2SO_4$
- ii: The amino group is protected, conveniently Z-protected, with reagents such as benzyloxycarbonyl chloride or succinimide in a suitable solvent such as dioxane in the presence of a base such as aqueous sodium hydroxide.
- iii: The carboxylic acid group is esterified, preferably with DBU and methl iodid in DMF to yield XXXIII.

XXXIII → XXXIV
- iv: Introduction of lower alkyl, substituted lower alkyl and aryl substituents ($R^6 = R^7$), e.g. by Palladium (0)- catalyzed Stille- (Stille, J. K. *Angew. Chem.* 1986, 68, 504) and Suzuki-couplings (Oh-e, T.; Mijaura, N.; Suzuki, A. *J. Org. Chem.* 1993, 58, 2201).

XXXIV → XXXV
- v: Removal of the Z-group of XXXIV, e.g. by hydrogenation using $H_2$ and a catalyst such as Palladium on charcoal in a suitable solvent such as ethanol, DMF or ethyl acetate.
- vi: Hydrolysis of the ester group, conveniently under acidic conditions, e.g. with 25% aqueous hydrochloric acid in a suitable solvent such as dioxane at an elevated temperature, conveniently at about 100° C.
- vii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield XXXV.

Reaction Scheme 9

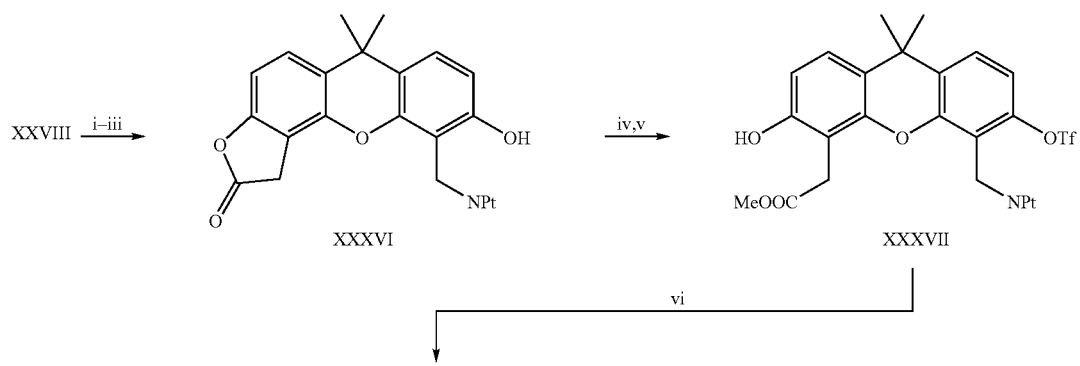

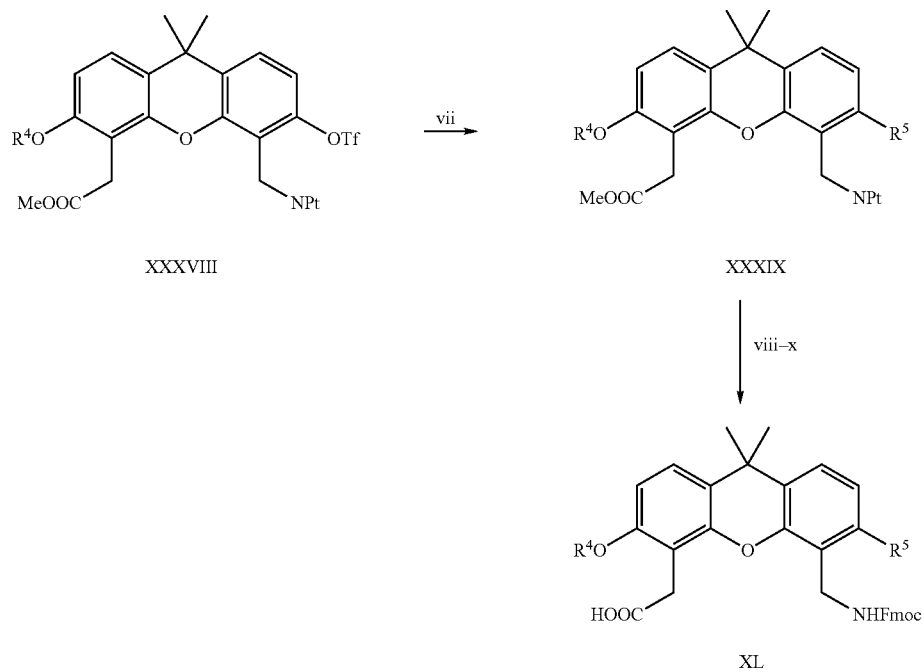

XXXVIII

XXXIX

XL

XXVIII ⟶ XXXVI i: Cleavage of the methoxy groups of XXVIII, preferably by treatment with an excess of boron tribromide in a suitable solvent such as dichloromethane.
ii: Hydrolysis of the cyano group under acidic conditions, preferably with 25% aqueous hydrochloric acid in a suitable solvent such as dioxane at an elevated temperature, conveniently at about 100° C.
iii: The resulting acid is treated with a dehydrating agent such as thionyl chloride in a suitable solvent such as dioxane yields XXXVI.

XXXVI ⟶ XXXVII iv: Treatment of XXXVI with an appropriate triflating reagent, preferably trifluorosulfonic acid anhydride in the presence of a base such as 2, 6-di-tert.-butyl-pyridine in a suitable solvent such as dichloromethane.
v: Heating of the intermediate, conveniently in a suitable solvent such as methanol.

XXXVII ⟶ XXXVIII vi: Introduction of lower alkyl or aryl-lower alkyl ($R^4$) by alkylation.

XXXVIII ⟶ XXXIX vii: Introduction of lower alkyl or aryl ($R^5$), conveniently by Palladium (0)- catalyzed Suzuki-coupling (Oh-e, T.; Mijaura, N.; Suzuki, A. *J. Org. Chem.* 1993, 58, 2001).

XXXIX ⟶ XL i: Cleavage of the methoxy groups of XXVIII, preferably by treatment with an excess of boron tribromide in a suitable solvent such as dichloromethane.
ii: Hydrolysis of the cyano group under acidic conditions, preferably with 25% aqueous hydrochloric acid in a suitable solvent such as dioxane at an elevated temperature, conveniently at about 100° C.
iii: The resulting acid is treated with a dehydrating agent such as thionyl chloride in a suitable solvent such as dioxane yields XXXVI.

Reaction Scheme 10

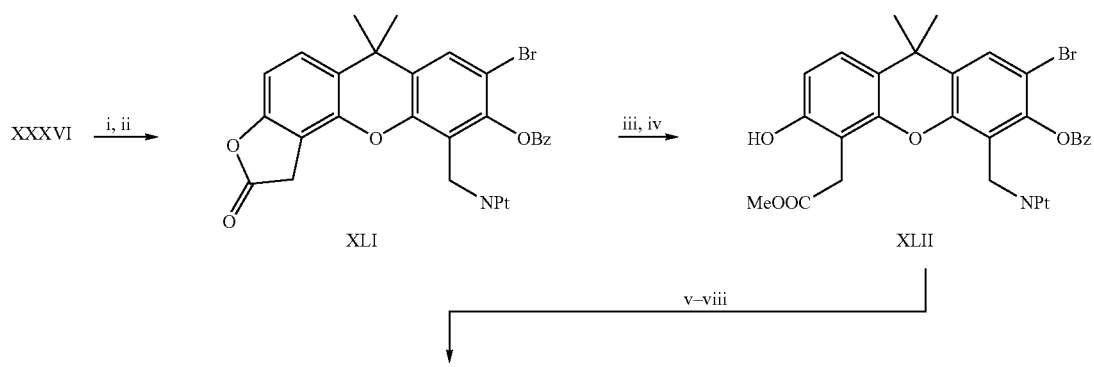

XXXVI →^{i, ii}→ XLI →^{iii, iv}→ XLII →^{v–viii}→

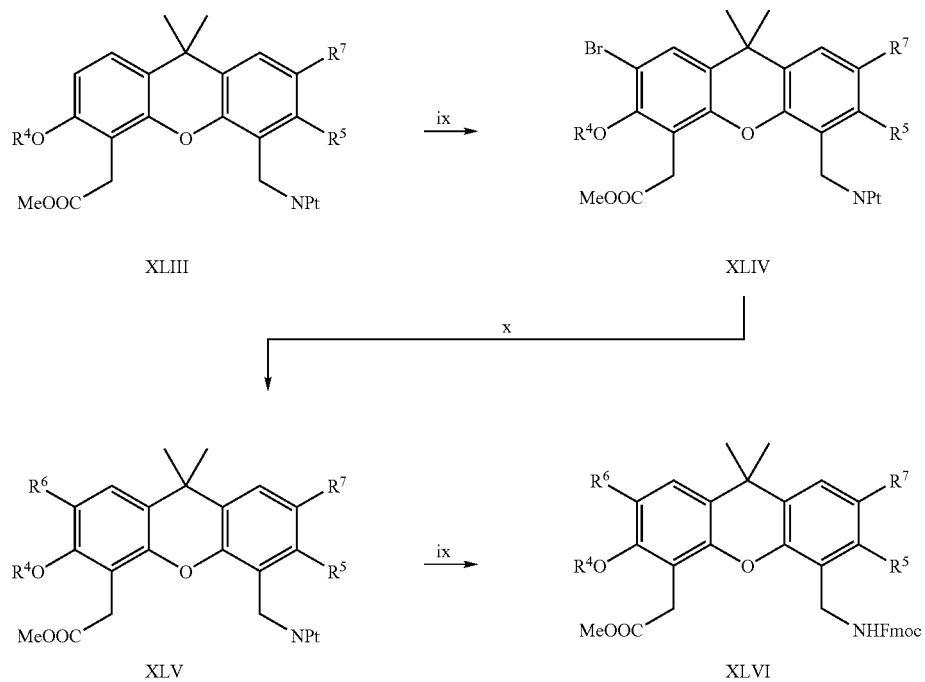

XXXVI ⟶ XLI i: Bromination of XXXVI using reagents such as bromine in a mixture of acetic acid and dichloromethane at temperatures ranging from about 0° C. to about room temperature.
ii: Benzoylation of the hydroxy group using an appropriate acylating agent such as benzoyl chloride or benzoic acid anhydride, a base such as pyridine or triethylamine and a suitable solvent such as dichloromethane.

XLI ⟶ XLII iii: XLI is treated with methanol and a catalytic amount of an acidic catalyst such as campher sulfonic acid under heating.
iv: Introduction of lower alkyl or aryl-lower alkyl ($R^4$) by alkylation using a base such as sodium hydride or potassium tert.-butoxide in a solvent such as tetrahydrofuran, dimethoxyethane or DMF.

XLII ⟶ XLIII v: Lower alkyl, substituted lower alkyl and aryl substituents ($R^7$) are involved, e.g. by Palladium(0)- catalyzed Stille- (Stille, J. K. *Angew. Chem.* 1986, 68, 504) and Suzuki- couplings (Oh-e, T.; Mijaura, N.; Suzuki, A. *J. Org. Chem.* 1993, 58, 2201).
vi: For cleaving the benzyloxy group the intermediate is conveniently heated with sodiumcyanide adsorbed on aluminum oxide and methanol.
vii: Treatment with an appropriate triflating reagent, preferably trifluorosulfonic acid anhydride, in the presence of a base such as 2,6-di-tert.-butyl-pyridine in a suitable solvent such as dichloromethane.
viii: Introduction of lower alkyl and aryl substituents ($R^5$), e.g. by Palladium(0)- catalyzed Stille- (Stille, J. K. *Angew. Chem.* 1986, 68, 504) and Suzuki- couplings (Oh-e, T.; Mijaura, N.; Suzuki, A. *J. Org. Chem.* 1993, 58, 2201).

XLIII ⟶ XLIV ix: Bromination under standard conditions such as using bromine in acetic acid and dichloromethane at temperatures ranging from about 0° C. to about room temperature.

XLIV ⟶ XLV x: Lower alkyl, substituted lower alkyl and aryl substituents ($R^6$) are introduced, e.g. by Palladium(0)- catalyzed Stille- (Stille, J. K. *Angew. Chem.* 1986, 68, 504) and Suzuki- couplings (Oh-e, T.; Mijaura, N.; Suzuki, A. *J. Org. Chem.* 1993, 58, 2201).

XLV ⟶ XLVI xi: The ester group is hydrolyzed under acidic conditions, conveniently with 25% aqueous hydrochloric acid in a suitable solvent such as dioxane at an elevated temperature, e.g. at about 100° C.
xii: The phthalimido group is cleaved, e.g. by hydrazinolysis, conveniently with hydrazine hydrate in a suitable solvent such as ethanol.
xiii: The intermediate free amino acid formed is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield XLVI.

Reaction Scheme 11

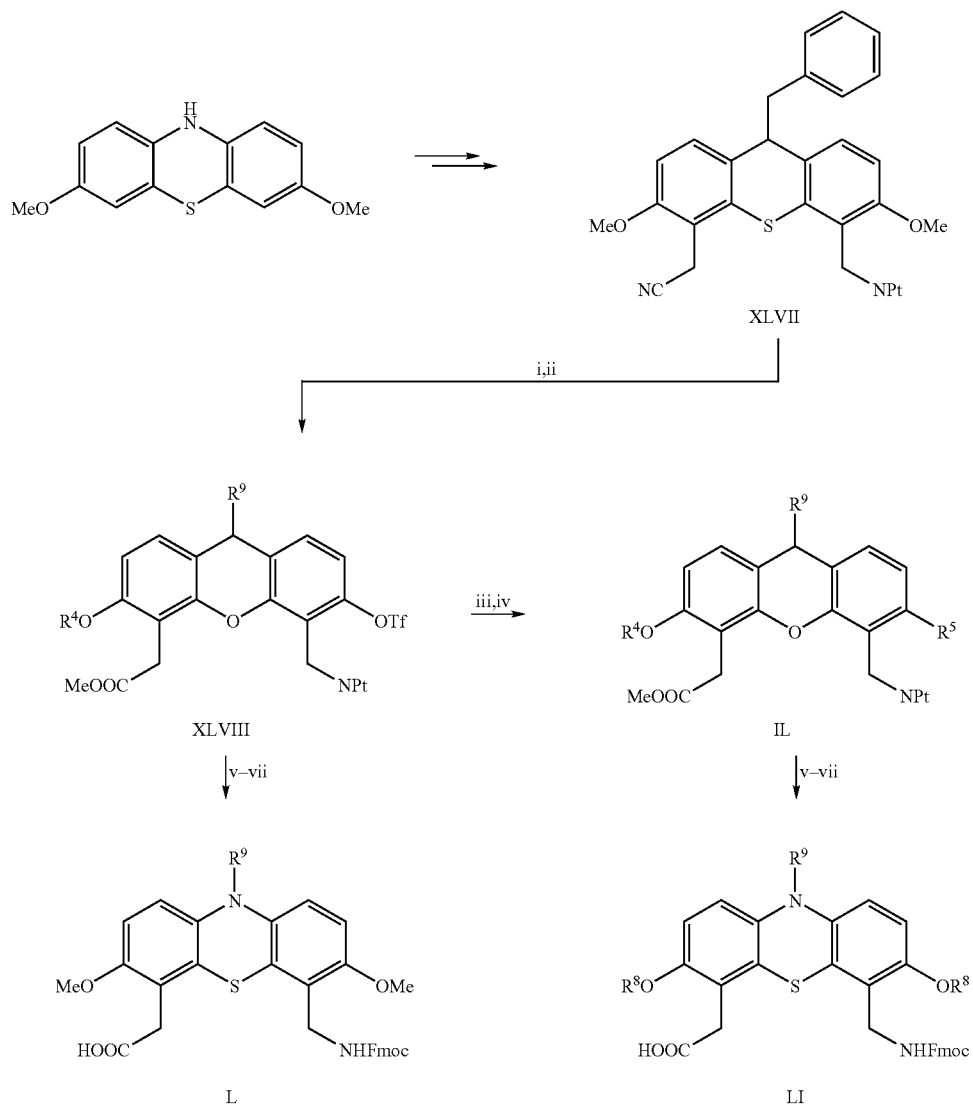

XLVII ⟶ XLVIII i: 3,7-Dimethoxyphenothiazine is prepared and converted into XLVII according to Müller, K.; Obrecht, D.; Knierzinger, A.; Spiegler, C.; Bannwarth, W.; Trzeciak, A.; Englert, G.; Labhardt, A.; Schönholzer, P. *Perspectives in Medicinal Chemistry*, Editor Testa, B.; Kyburz, E.; Fuhrer, W.; Giger, R., Weinheim, New York, Basel, Cambridge: Verlag Helvetica Chimica Acta, 1993, 513–531; Bannwarth, W.; Gerber, F.; Grieder, A.; Knierzinger, A.; Müller, K.; Obrecht. D.; Trzeciak, A. *Can. Pat. Appl.* CA2101599(131 pages). The benzyl group is cleaved off from XLVII conveniently by hydrogenation, e.g. with $H_2$ and a catalyst such as Palladium on charcoal in a suitable solvent such as ethanol, DMF or ethyl acetate.

ii: Introduction of lower alkyl ($R^9$) by alkylation using an appropriate alkylating agent ($R^9$-X'; X' = OTf, Br, I) and strong bases such as sodium amide in liquid nitrogen or sodium hydride in tetrahydrofuran, dioxane or DMF in the presence of a phase transfer catalyst such as TDA-I. In a similar manner substituted lower alkyl ($R^9$) can be introduced; thus, for example $R^9 = CH_2COOR^{10}$ and $CH_2CH_2COOR^{10}$ can be introduced by treatment with the appropriate 2-halo acetic and, respectively, 3-halo propionic acid derivatives.

XLVIII ⟶ IL iii: Cleavage of the methoxy groups of XLVIII, conveniently by treatment with an excess of boron tribromide in a suitable solvent such as dichloromethane at temperatures ranging from about -20° C. to about room temperature.

iv: For the introduction of lower alkyl, substituted lower alkyl or aryl-lower alkyl substituents ($R^8$) the intermediate bis-phenol derivative is conveniently reacted with a reagent of the formula $R^8$-X' (X' = OTf, Br, I) in the presence of strong bases such as sodium hydride in tetrahydrofuran, dioxan or DMF in the presence of a phase transfer catalyst such as TDA-I.

XLVIII ⟶ L  IL ⟶ LI v: The cyano group of XLVIII and, respectively, IL is hydrolyzed, conveniently under acidic conditions, e.g. with 25% aqueous hydrochloric acid in a suitable solvent such as dioxane at an elevated temperature, e.g. at about 100° C.

vi: The phthalimide group of the intermediate is cleaved, conveniently by hydrazinolysis, e.g. with hydrazine hydrate in a suitable solvent such as ethanol.

vii: The free amino group is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield L and respectively, LI.

Reaction Scheme 12

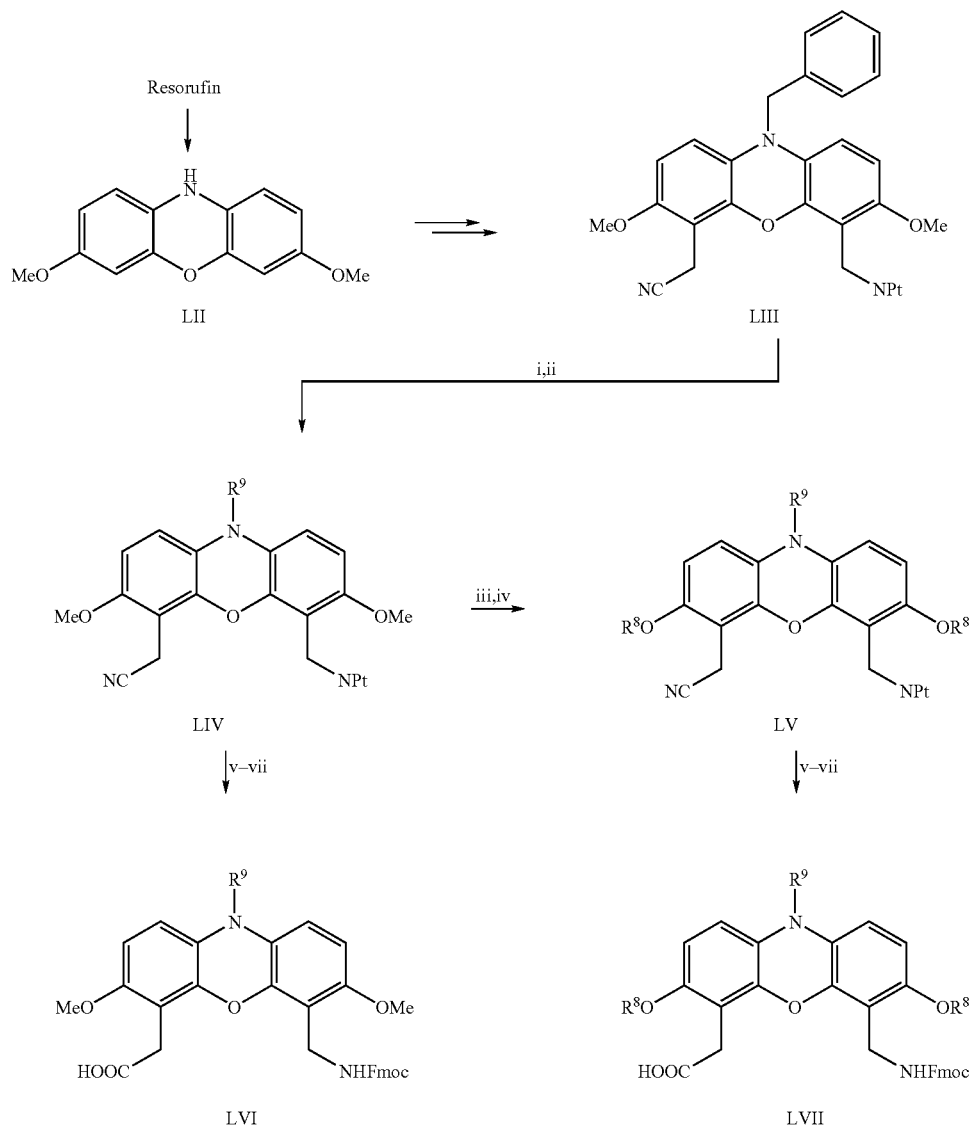

LIII ⟶ LIV i: LII can be prepared from commercial resorufin and coverted into LIII according to Müller, K.; Obrecht, D.; Knierzinger, A.; Spiegler, C.; Bannwarth, W.; Trzeciak, A.; Englert, G.; Labhardt, A.; Schönholzer, P. *Perspectives in Medicinal Chemistry*, Editor Testa, B.; Kyburz, E.; Fuhrer, W.; Giger, R., Weinheim, New York, Basel, Cambridge:Verlag Helvetica Chimica Acta, 1993, 513–531; Bannwarth, W.; Gerber, F.; Grieder, F.; Grieder, A.; Knierzinger, A.; Müller, K.; Obrecht. D.; Trzeciak, A. Can. Pat. Appl. CA2101599(131 pages). For splitting off the benzyl group LIII is conveniently hydrogenated e.g. with $H_2$ and a catalyst such as Palladium on charcoal in a suitable solvent such as ethanol, DMF or ethyl acetate.

ii: Introduction of lower alkyl ($R^9$) by alkylation with $R^9$-X' (X' = OTf, Br, I) using strong bases such as sodium amide in liquid nitrogen or sodium hydride in tetrahydrofuran, dioxan or DMF in the presence of a phase transfer catalyst such as TDA-I to yield LIV. In a similar manner substituted lower alkyl ($R^9$) can be introduced; thus, for example, $R^9 = CH_2COOR^{10}$ and $CH_2CH_2COOR^{10}$ can be introduced by treatment with the appropriate 2-halo acetic and, respectively, 3-halo propionic acid derivatives.

LIV ⟶ LV iii: Cleavage of the methoxy groups of LIV, conveniently by treatment with an excess boron tribromide in dichloromethane at temperatures ranging from about -20° C. to about room temperature.

iv: The intermediate bis-phenol derivative is preferably reacted with $R^8$-X' (X' = OTf, Br, I) in the presence of strong bases such as sodium hydride in tetrahydrofuran, dioxan or DMF in the presence of a phase transfer catalyst such as TDA-I.

LIV ⟶ LVI   LV ⟶ LVII v: The cyano group of LIV and, respectively, LV is hydrolyzed under acidic conditions, e.g. with 25% aqueous hydrochloric acid in a suitable solvent such as dioxane at an elevated temperature, conveniently at about 100° C.

vi: The phthalimide group is cleaved, conveniently by hydrazinolysis, e.g. with hydrazine hydrate in a suitable solvent such as ethanol.

vii: The free amino group is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield LVI and respectively, LVII.

The following Examples illustrate the invention in more detail but are not intended to limit its scope in any manner.

EXAMPLE 1

Preparation of a Single Compound of Formula I 1,4 g of 2-chlorotrityl chloride resin (125 mmol/g, 1.75 mmol) were filled into a three necked flask. The resin was suspended in DCM (14 ml) and allowed to swell at room temperature under constant stirring. The resin was treated with 1.25 g (1.077 equiv.) of Fmoc-Arg(Pmc)-OH and 0.898 ml of diisopropylethylamine (DIPEA) in DCM (10 ml), the mixture was shaken at 25° C. for 15 minutes, poured into the pre-swollen resin and stirred at 25° C. for 18 hours. The resin colour changed to purple and the solution remained yellowish. The resin was washed extensively and dried at 40° C. under vacuum for 4 hours.

| Yield: 2.379 gm | Loading: 84% |
|---|---|

The esterified resin was then subjected to the following synthesis cycle→40 mg per reaction vessel.

| Step | Reagent | Time |
|---|---|---|
| 1 | DCM, swell and wash | 3 × 1 min. |
| 2 | 20% piperidine/DMF | 1 × 15 min. |
| 3 | DMF, wash and swell | 5 × 1 min. |
| 4 | 4 equiv. Fmoc amino acid/DMF + 4 equiv. 1-benzotriazol-1-yl-tetramethyluronium hexafluoro phosphate (HBTU) + 4 equiv. 1-hydroxybenzotriazole (HOBt) + 6 equiv. Diisopropylethylamine | 1 × 120 min. |
| 5 | DMF, wash | 3 × 1 min. |
| 6 | Isopropylalcohol, wash | 2 × 1 min. |
| 7 | DCM, wash | 2 × 1 min. |

5 ml of the solvent were used in each step. Fmoc-Val-OH, Fmoc-Ile-OH, Fmoc-Glu(Otu)-OH, Fmoc-L-Pro-OH, Fmoc-D-Pro-OH, Fmoc-Ile-OH, Fmoc-Pro-OH, Fmoc-Lys(Boc)-OH and Fmoc-Lys(Boc)-OH were coupled according to the above protocol.

Cleavage of the Fully Protected Peptide Fragment

After completion of the synthesis, the peptide resin was suspended in 5 ml of 1% TFA in DCM (v/v) and agitated for 10 minutes, whereupon the resin was filtered off and the filtrate was neutralized with pyridine (1 equiv.). This procedure was repeated twice to ensure completion of the cleavage. The filtrate was evaporated to dryness and analyzed by reverse phase (RP)-HPLC to monitor the efficiency of the linear peptide synthesis.

Cyclization of the H-Lys(Boc)-Lys(Boc)-Pro-Ile-Pro-D-Pro-L-Pro-Glu(OtBu)-Ile-Val-Arg(Pmc)-OH Linear Peptide [SEQ ID NO:31]

50 mg (0.0294 mmol) of the fully protected linear peptide were dissolved in DMF (50 ml, conc. 1 mg/ml). Then 33.5 mg (0.0882 mMol, 3 equiv.) of HATU, 12.0 mg (0.0882 mMol, 3 eq) of HOAt and 5 ml of DIPEA (1% v/v) were added and the mixture was stirred at 20° C. for 16 hours and subsequently concentrated in a vacuum. The residue was partitioned between dichloromethane (DCM) and H$_2$O/ CH$_3$CN (90:10). The DCM phase was evaporated to yield the pure fully protected cyclic peptide.

Deprotection of the Cyclic Peptide:

The amorphous powder obtained was dissolved in 2 ml of the cleavage mixture containing 95% trifluoroacetic acid, 2.5% water and 2.5% triisopropyl siliane (TIS). The mixture was left to stand at 20° C. for 2 hours and then concentrated in a vacuum. The residue was triturated with diethyl ether, and 20 mg of compound 1 [SEQ ID NO:32] were obtained as a white colored powder.

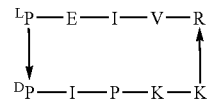

1

$C_{55}H_{95}N_{15}O_{12}$, MW 1158.5

| MS(ESI): | 580.02 (M + 2H$^+$)$^{2+}$, 387.02 (M + 3H$^+$)$^{3+}$ |
|---|---|
| HPLC-RT(min.): | 7.51 |
| Conditions: | Analytical HPLC-conditions: column CC 250/4 Nucleosil 100-5 Protect 1 (Ser. No. 8111346, Batch 8023); gradient 5% acetonitril/water(0.1% trifluoroacetic acid to 100% acetonitril in 15 minutes; stay constant for 5 minutes and return to 5% acetonitril/water(0.1% trifluoroacetic acid) in 5 minutes. |

EXAMPLE 2

Preparation of a Single Compound of Formula I

By a procedure analogous to that described in Example 1, Fmoc-Val-OH, Fmoc-Tyr(tBu)-OH, Fmoc-Glu(OtBu)-OH, Fmoc-$^L$Pro-OH, Fmoc$^D$-Pro-OH, Fmoc-Ile-OH, Fmoc-Tyr(tBu)-OH, Fmoc-Lys(Boc)-OH and Fmoc-Lys(Boc)-OH were coupled to the Fmoc-Arg(Pmc)-OH loaded resin, cleaved, cyclised and deprotected to yield compound 2 [SEQ ID NO:33]:

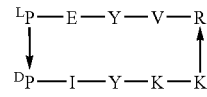

2

$C_{62}H_{95}N_{15}O_{14}$, MW 1274.5

| MS(ESI): | 638.4 (M + 2H$^+$)$^{2+}$, 424.8.02 (M + 3H$^+$)$^{3+}$ |
|---|---|
| HPLC-RT(min.): | 8.59 |
| Conditions: | Analytical HPLC-conditions: column CC 250/4 Nucleosil 100-5 Protect 1 (Ser. No. 8111346, Batch 8023); gradient: 5% acetonitril/water(0.1% trifluoroacetic acid to 100% acetonitril in 15 minutes; stay constant for 5 minutes and return to 5% acetonitril/water(0.1% trifluoroacetic acid) in 5 minutes. |

EXAMPLE 3

Preparation of a Single Compound of Formula I

By a procedure analogous to that described in Example 1, Fmoc-Val-OH, Fmoc-Trp-OH, Fmoc-Glu(OtBu)-OH, Fmoc-$^L$Pro-OH, Fmoc-$^D$Pro-OH, Fmoc-Ile-OH, Fmoc-Trp-OH, Fmoc-Lys(Boc)-OH and Fmoc-Lys(Boc)-OH were coupled to the Fmoc-Arg(Pmc)-OH loaded resin, cleaved, cyclised and deprotected to yield compound 3 [SEQ ID NO:34]:

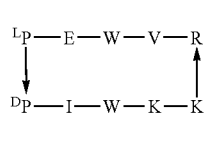

3

$C_{66}H_{97}N_{17}O_{12}$, MW 1320.6

| | |
|---|---|
| MS(ESI): | 1321.6 (M + H$^+$)$^+$ |
| HPLC-RT(min.): | 9.04 |
| Conditions: | Analytical HPLC-conditions: column CC 250/4 Nucleosil 100-5 Protect 1 (Ser. No 8111346, Batch 8023); gradient: 5% acetonitril/water(0.1% trifluoroacetic acid to 100% acetonitril in 15 minutes; stay constant for 5 minutes and return to 5% acetonitril/water(0.1% trifluoroacetic acid) in 5 minutes. |

EXAMPLE 4

Preparation of a Single Compound of Formula I

By a procedure analogous to that described in Example 1, Fmoc-Val-OH, Fmoc-Ala-OH, Fmoc-Glu(OtBu)-OH, Fmoc-$^L$Pro-OH, Fmoc-$^D$Pro-OH, Fmoc-Ile-OH, Fmoc-Ala-OH, Fmoc-Lys(Boc)-OH and Fmoc-Lys(Boc)-OH were coupled to the Fmoc-Arg(Pmc)-OH loaded resin, cleaved, cyclised and deprotected to yield compound 4 [SEQ ID NO:35]:

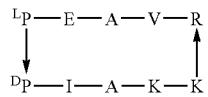

4

$C_{50}H_{87}N_{15}O_{12}$, MW 1090.5

| | |
|---|---|
| MS(ESI): | 546.15.4 (M + 2H$^+$)$^{2+}$, 364.3 (M + 3H$^+$)$^{3+}$ |
| HPLC-RT(min.): | 12.51 |
| Conditions: | Analytical HPLC-conditions: column CC 250/4 Nucleosil 100-5 Protect 1 (Ser. No. 8111346, Batch 8023); gradient: 5% acetonitril/water(0.1% trifluoroacetic acid to 100% acetonitril in 15 minutes; stay constant for 5 minutes and return to 5% acetonitril/water(0.1% trifluoroacetic acid) in 5 minutes. |

EXAMPLE 5

Preparation of a Single Compound of Formula I

By a procedure analogous to that described in Example 1, Fmoc-Val-OH, Fmoc-Ser(OtBu)-OH, Fmoc-Glu(OtBu)-OH, Fmoc-$^L$Pro-OH, Fmoc-$^D$Pro-OH, Fmoc-Ile-OH, Fmoc-Ser(OtBu)-OH, Fmoc-Lys(Boc)-OH and Fmoc-Lys(Boc)-OH were coupled to the Fmoc-Arg(Pmc)-OH loaded resin, cleaved, cyclised and deprotected to yield compound 5 (SEQ ID NO:36]:

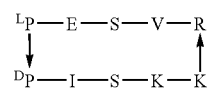

5

$C_{50}H_{87}N_{15}O_{14}$, MW 1122.3

| | |
|---|---|
| MS(ESI): | 562.15 (M + 2H$^+$)$^{2+}$, 375.3 (M + 3H$^+$)$^+$ |
| HPLC-RT(min.): | 5.74 |
| Conditions: | Analytical HPLC-conditions: column CC 250/4 Nucleosil 100-5 Protect 1 (Ser. No. 8111346, Batch 8023); gradient: 5% acetonitril/water(0.1% trifluoroacetic acid to 100% acetonitril in 15 minutes; stay constant for 5 minutes and return to 5% acetonitril/water(0.1% trifluoroacetic acid) in 5 minutes. |

EXAMPLE 6

Synthesis of a Library of Compounds of Formula I for Mimicking the PDGF-loop-III on a Diproline Template and Testing thereof in a Solid-Phase Assay 1. Target Peptides $x_1$–$x_4$: variable amino acid residues (x)

ValArgLysLys (VRKK) [SEQ ID NO:1]: constant amino acid residues $^D$Pro$^L$Pro: template

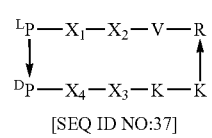

[SEQ ID NO:37]

$x_1^{1-4}$: Glu, Tyr, Trp, Ala $x_2^{1-6}$: Ile, Tyr, Trp, Ala, Ser, Lys $x_3^{1-6}$: Pro, Tyr, Trp, Ala, Ser, Lys $x_4^{1-4}$: Ile, Tyr, Trp, Ala

TABLE 1

The sequences of the 24 target cyclic peptides (the first five corresponding to those obtained according to Examples 1–5)

| | $x_1^1x_4^1$ (E-I) | $x_1^2x_4^2$ (Y-Y) | $x_1^3x_4^3$ (W-W) | $x_1^4x_4^4$ (A-A) |
|---|---|---|---|---|
| $x_2^1x_3^1$ (I-P) | 1<br>$^L$P-E-I-V-R<br>$^D$P-I-P-K-K<br>[SEQ ID NO: 32] | 7<br>$^L$P-Y-I-V-R<br>$^D$P-V-P-K-K<br>[SEQ ID NO: 39] | 13<br>$^L$P-W-I-V-R<br>$^D$P-W-P-K-K<br>[SEQ ID NO: 45] | 19<br>$^L$P-A-I-V-R<br>$^D$P-A-P-K-K<br>[SEQ ID NO: 51] |
| $x_2^2x_3^2$ (Y-Y) | 2<br>$^L$P-E-Y-V-R<br>$^D$P-I-Y-K-K<br>[SEQ ID NO: 33] | 8<br>$^L$P-Y-Y-V-R<br>$^D$P-Y-Y-K-K<br>[SEQ ID NO: 40] | 14<br>$^L$P-W-Y-V-R<br>$^D$P-W-Y-K-K<br>[SEQ ID NO: 46] | 20<br>$^L$P-A-Y-V-R<br>$^D$P-A-Y-K-K<br>[SEQ ID NO: 52] |
| $x_2^3x_3^3$ (W-W) | 3<br>$^L$P-E-W-V-R<br>$^D$P-I-W-K-K<br>[SEQ ID NO: 34] | 9<br>$^L$P-Y-W-V-R<br>$^D$P-Y-W-K-K<br>[SEQ ID NO: 41] | 15<br>$^L$P-W-W-V-R<br>$^D$P-W-W-K-K<br>[SEQ ID NO: 47] | 21<br>$^L$P-A-W-V-R<br>$^D$P-A-W-K-K<br>[SEQ ID NO: 53] |
| $x_2^4x_3^4$ (A-A) | 4<br>$^L$P-E-A-V-R<br>$^D$P-I-A-K-K<br>[SEQ ID NO: 35] | 10<br>$^L$P-Y-A-V-R<br>$^D$P-Y-A-K-K<br>[SEQ ID NO: 42] | 16<br>$^L$P-W-A-V-R<br>$^D$P-W-A-K-K<br>[SEQ ID NO: 48] | 22<br>L-P-A-A-V-R<br>D-P-A-A-K-K<br>[SEQ ID NO: 54] |
| $x_2^5x_3^5$ (S-S) | 5<br>$^L$P-E-S-V-R<br>$^D$P-I-S-K-K<br>[SEQ ID NO: 36] | 11<br>$^L$P-Y-S-V-R<br>$^D$P-Y-S-K-K<br>[SEQ ID NO: 43] | 17<br>$^L$P-W-S-V-R<br>$^D$P-W-S-K-K<br>[SEQ ID NO: 49] | 23<br>$^L$P-A-S-V-R<br>$^D$P-A-S-K-K<br>[SEQ ID NO: 55] |
| $x_2^6x_3^6$ (K-K) | 6<br>$^L$P-E-K-V-R<br>$^D$P-I-K-K-K<br>[SEQ ID NO: 38] | 12<br>$^L$P-Y-K-V-R<br>$^D$P-Y-K-K-K<br>[SEQ ID NO: 44] | 18<br>$^L$P-W-K-V-R<br>$^D$P-W-K-K-K<br>[SEQ ID NO: 50] | 24<br>$^L$P-A-K-V-R<br>$^D$P-A-K-K-K<br>[SEQ ID NO: 56] |

2. Experimental Procedures:

2.1. Synthesis of Protected Linear Peptides

The first amino acid Fmoc-Arg(Pmc)-OH (1 eq.) was linked to 2-chlorotrityl chloride resin (Polyphor, 1.25 mmol/g) with 3 eq. DIEA in DCM overnight, the attachment was ca.85%. The linear peptides were assembled using standard Fmoc chemistry, 4 eq. each of amino acids, of HBTU and HOBt and 6 eq. of DIEA in DMF being used and the coupling time being 1.5–2 h. The protected linear peptides were cleaved from the resin with 1% TFA in DCM (2×10 min.) and neutralizd with pyridine (1 eq.), then the solvent was evaporated.

2.2. Cyclisation of Protected Linear Peptides

The protected linear peptide (without purification) was directly cyclized at a concentration of 1.0 mg/ml in DMF using HATU (3 eq.), HOAt (3 eq.) and DIEA (1% v/v) for 16 h. Then DMF and DIEA were evaporated, the residue was dissolved in DCM, the solution was extracted with $H_2O/CH_3CN$ (90:10), and afterwards the DCM was removed.

2.3. Deprotection of the Cyclized Peptides

The cyclization product was treated with 95% TFA, 2.5% $H_2O$ and 2.5% TIS for 2 h, then most of the TFA was evaporated. $Et_2O$ was added to precipitate the product. After centrifugation, the ether was carefully removed and the final product was obtained after drying under reduced pressure. Depending on its purity, the product was purified by preparative HPLC.

2.4. Solid-Phase Assay

Direct immobilization of platelet-derived growth factor β-receptor (PDGFR-β) was performed by overnight incubation in immunosorbent 96-well plates (Nunc) at 4° C. using 100 ng of purified protein in 100 µl of 15 mM $Na_2CO_3$, 35 mM $NaHCO_3$, pH 9.6. Plates were washed once with Tris buffered saline (TBS, 20 mM Tris-HCl, 15 mM Na Cl, pH 7.4), and nonspecific adsorption was blocked by at least 1 h of incubation with TBS plus 1% bovine serum albumin (BSA). Following washing with TBS plus 0.1% Tween, 3000 cpm of $^{125}$I-PDGF-BB and increasing amounts of unlabeled PDGF-BB or the peptides to be tested were added to duplicate wells and incubated for 3 h at room temperature in TBS plus 0.1% Tween, 1 mM $CaCl_2$, 1 mM $MgCl_2$, and 1% BSA. The plates were washed three times with TBS plus 0.1% Tween, and the bound ligand was removed with 0.1 M citric acid, pH 2.5, before counting in a γ-counter.

3. Results

The cyclic peptides were analyzed and purified by preparative HPLC (dual-pump Pharmacia system with Waters RCM-µBondapak™-$C_{18}$-cartridges, 10 µm 300 A 25×100 mm for prep. and 8×100 mm for anal., with flow rates of 8 and 2 ml/mim, respectively; UV detection at 226 and 278 nm), then MS, NMR(600 MHz,1H) and CD. Solid-phase assays were run, as described in 2.4.

4. Discussion 4.1. Linear Peptides were Analyzed by HPLC, All of the 24 Compounds Turned out to be Pure, >95% Indicating that the Assembling of Amino Acids Worked Performed Reliably.

4.2 Cyclized Peptides a) The linear peptides cleaved from resin, neutralized with pyridine to form pyridine salts, which needed not to be purified before their cyclization.
b) Different concentrations of peptides for cyclization were compared, 1 mg, 2 mg, 5 mg, 10 mg, 20 mg/ml DMF, the 1 mg/ml concentration gave the best result
c) The purities of the crude products are shown in Table 2.

4.3. Solid-Phase Assay

The $IC_{50}$-values are shown in Table 2. The differences in $IC_{50}$-values between the crude and purified peptides were only marginal.

TABLE 2

Summary of Examples 1–24

| Target peptide | Formula M.W. | ESI-MS $[M + H^+]^+$; $[M + 2H^+]^{2+}$; $[M + 3H^+]^{3+}$ | Retention time of HPLC (min) | Purity of crude product | Assay $I_{50}$ (μM) |
|---|---|---|---|---|---|
| 1 | $C_{55}H_{95}N_{15}O_{12}$ 1158.5 | 580.02; 387.02 | 7.51 | 95% | 2200 |
| 2 | $C_{62}H_{95}N_{15}O_{14}$ 1274.5 | 1274.8; 638.01; 425.75 | 8.59 | 95% | 2000 |
| 3 | $C_{66}H_{97}N_{17}O_{12}$ 1320.6 | 1320.81; 661.06; 441.11 | 9.04 | 80% | 1500 |
| 4 | $C_{50}H_{87}N_{15}O_{12}$ 1090.3 | 1090.54; 545.83; 364.26 | 12.5 | 90% | >2500 |
| 5 | $C_{50}H_{87}N_{15}O_{14}$ 1122.3 | 1122.71; 562.07; 375.05 | 5.74 | 95% | 2500 |
| 6 | $C_{56}H_{101}N_{17}O_{12}$ 1204.5 | 1205.7; 603.18; 402.58 | 9.90 | 95% | >2500 |
| 7 | $C_{62}H_{95}N_{15}O_{12}$ 1242.5 | 621.90; 414.89 | 9.14 | 95% | 1500 |
| 8 | $C_{69}H_{95}N_{15}O_{14}$ 1358.6 | 679.82; 453.61 | 9.42 | 95% | 800 |
| 9 | $C_{73}H_{97}N_{17}O_{12}$ 1404.7 | 1404.83; 703.08; 469.16 | 9.71 | 65% | 500 |
| 10 | $C_{57}H_{87}N_{15}O_{12}$ 1174.4 | 1174.73; 587.97; 392.39 | 9.09 | 90% | 2000 |
| 11 | $C_{57}H_{87}N_{15}O_{14}$ 1206.4 | 1206.75; 604.02; 403.01 | 9.10 | 90% | 2000 |
| 12 | $C_{63}H_{101}N_{17}O_{12}$ 1288.6 | 1288.92; 645.06; 430.47 | 8.59 | 90% | 1500 |
| 13 | $C_{66}H_{97}N_{17}O_{10}$ 1288.6 | 1288.82; 645.08; 430.47 | 8.27 | 95% | 260 |
| 14 | $C_{73}H_{97}N_{17}O_{12}$ 1404.7 | 1405.0; 703.09; 469.08 | 9.26 | 90% | 170 |
| 15 | $C_{77}H_{99}N_{19}O_{10}$ 1450.8 | 1451.06; 726.06; 484.42 | 10.35 | 20% | |
| 16 | $C_{61}H_{89}N_{17}O_{10}$ 1220.5 | 1220.87; 611.03; 407.74 | 9.81 | 90% | 800 |
| 17 | $C_{61}H_{89}N_{17}O_{12}$ 1252.5 | 1252.85; 627.03; 418.46 | 9.84 | 90% | 800 |
| 18 | $C_{67}H_{103}N_{19}O_{10}$ 1334.7 | 1334.78; 668.15; 445.80 | 9.10 | 90% | 500 |
| 19 | $C_{50}H_{87}N_{15}O_{10}$ 1058.3 | 1058.84; 530.03; 353.69 | 7.86 | 95% | >2500 |
| 20 | $C_{57}H_{87}N_{15}O_{12}$ 1174.4 | 1174.71; 588.11; 392.41 | 8.20 | 60% | 2500 |
| 21 | $C_{61}H_{89}N_{17}O_{10}$ 1220.5 | 1220.91; 611.16; 407.78 | 8.85 | 30% | 2000 |
| 22 | $C_{45}H_{79}N_{15}O_{10}$ 990.2 | 495.7 | 6.77 | 85% | >2500 |
| 23 | $C_{45}H_{79}N_{15}O_{12}$ 1022.2 | 511.94 | 7.12 | 85% | 2500 |
| 24 | $C_{51}H_{93}N_{17}O_{10}$ 1104.4 | 553.12 | 6.86 | 90% | 2500 |

Analytical HPLC-conditions: column CC 250/4 Nucleosil 100-5 Protect 1 (Ser. No. 8111346, Batch 8023); gradient: 5% acetonitril/water(0.1% trifluoroacetic acid to 100% acetonitril in 15 minutes; stay constant for 5 minutes and return to 5% acetonitril/water(0.1% trifluoroacetic acid) in 5 minutes.

EXAMPLES 25–40

The following Examples describe the application of the process to the synthesis of 6-mer, 8-mer, 10mer, 12-mer, 14-mer and 16-mer β-hairpin loop mimetics incorporating three different templates and a common key motif-$k^1$-$x^1$-template-$x^2$-$k^2$-[SEQ ID NO:57] where $x^1$=Y, F, K or W, $x^2$=Y, $k^1$=K and $k^2$=E. Due to the β-hairpin structure $x^1$ and $x^2$ are lying on the same side of the β-sheet and form a hydrophobic patch. Such motifs are present e.g. in various chemokines (see Tarby, C. M.; Saunders, J. *Drug Discovery Today* 1999, 4, 80–92; Ponath, P. D. *Exp. Opin. Invest. Drugs* 1998, 7, 1–16).

1. Synthesis of (2S,6S,8aS,8a-{[(tert.-butyl)oxycarbonyl]methyl}perhydro-5,8-dioxo-{[(9H-fluoren-9-yl)methoxycarbonyl]amino}-pyrrolo[1,2-a]pyrazine-6-acetic acid (Template b1)

To a stirred solution of 250 mg (0.414 mmol) of allyl{(2S,6S,8aS)-8a-[(tert.-butyl)oxycarbonyl]methyl}perhydro-5,8-dioxo-{[(9H-fluoren-9-yl)methoxycarbonyl]amino}-pyrrolo[1,2-a]pyrazin-6-acetate in a degassed mixture of dichloromethane/methanol (9:1, 3 ml) were added under argon 25 mg (0.0216 mmol) of tetrakis(triphenylphosphine) palladium, 0.05 ml of acetic acid and 0.025 ml of N-methylmorpholin. The reaction mixture was stirred for 48 hours at room temperature and poured onto water and dichloromethane. The organic phase was dried (MgSO$_4$), evaporated and the residue chromatographed on SiO$_2$ with dichloromethane/methanol (9:1) to yield 180 mg (77%) of (2S,6S,8aS)-8a-{[(tert-butyl)oxycarbonyl]methyl}perhydro-5,8dioxo-{[(9H-fluoren-9-yl)-methoxycarbonyl]amino}-pyrrolo[1,2-a]pyrazine-6-acetic acid (template b1) as a white powder.

$^1$H-NMR(300MHz, DMSO-d$_6$): 8.30 (s, 1H); 7.88 (d, J=7.2, 2H); 7.67 (d, J=7.4, 2H); 7.62 (br.s, 1H); 7.41 (t, J=7.2, 2H); 7.33 (t, J=7.4, 2H); 4.35–4.2 (m, 5H); 3.55 (br.d, J=6.3, 2H); 2.8–2.55 (m, 3H); 2.45–2.25 (m, 2H); 2.1–1.95 (m, 1H); 1.35 (s, 9H); MS(ESI): 586.1 (M+Na)$^+$, 564.1 (M+H)$^+$.

2. Synthesis of Linear Peptides:

The first amino acid Fmoc-Arg(Pmc)-OH (1 eq.) was linked to 2-chlorotrityl chloride resin (Polyphor, 1.25 mmol/g) with 3 eq. DIEA in DCM overnight, the attachment was ca.80%. The linear peptides were assembled using standard Fmoc chemistry, 4 eq. each of amino acids and of the template (or, if appropriate, of Fmoc-$^L$Pro-OH and of Fmoc-$^D$Pro-OH), 4eq. each of HBTU and HOBt and 6 eq. of DIEA in DMF being used and the coupling time being 1.5–2 h. The protected linear peptides were cleaved from the resin with 1% TFA in DCM (4×10 min.) and neutralized with pyridine (1 eq.), then the solvent was evaporated.

3. Cyclisation of the Linear Peptides

The protected linear peptide (without purification) was directly cyclized at a concentration of 1.0 mg/ml in DMF using HATU (3 eq.), HOAt (3 eq.) and DIEA (1% v/v) for 16 h. Then DMF and DIEA were evaporated, the residue was dissolved in DCM, the solution was extracted with H$_2$O/CH$_3$CN (90:10), and afterwards the DCM was removed.

4. Deprotection of the Cyclized Peptides

The cyclization product was treated with 95% TFA, 2.5% H$_2$O and 2.5% TIS for 2 h, then most of the TFA was evaporated. Et$_2$O was added to precipitate the product. After centrifugation, the ether was carefully removed and the final product was obtained after drying under reduced pressure. Depending on its purity, the product was purified by preparative HPLC.

The following templates were used.

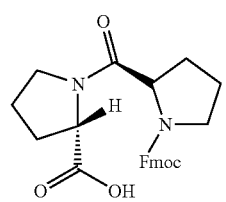

Template a1

($^D$Pro-$^L$Pro)

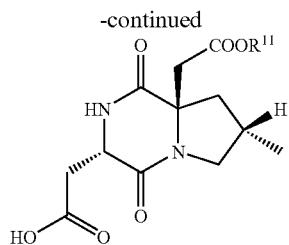

Template b1 (R$^{11}$ = tBU)
Template b2 (R$^{11}$ = H)

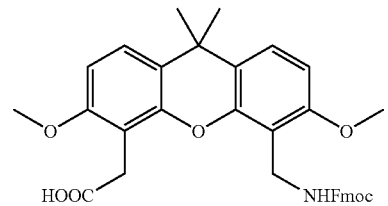

Template f1

EXAMPLE 25

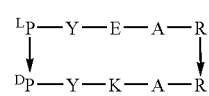

25

By a procedure analogous to that described in Example 1, Fmoc-Ala-OH, Fmoc-Glu(OtBu)-OH, Fmoc-Tyr(tBu)-OH, Fmoc-$^L$Pro-OH, Fmoc-$^D$Pro-OH, Fmoc-Tyr(tBu)-OH, Fmoc-Lys(Boc)-OH, Fmoc-Ala-OH and Fmoc-Arg(Pmc)-OH were coupled to the Fmoc-Arg(Pmc)-OH loaded resin, cleaved, cyclised and deprotected to yield compound 25 [SEQ ID NO:58].

| | |
|---|---|
| MW: | C$_{57}$H$_{85}$N$_{17}$O$_{14}$; [1232.30] |
| MS(ESI): | 616.72 [M + 2H$^+$]$^{2+}$ |
| HPLC-RT(min.): | 10.83 |
| Conditions: | Analytical HPLC-conditions: column CC 250/4 Nucleosil 100-5 Protect 1 (Ser. No. 8111346, Batch 8023); gradient 10% acetonitril/ 90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 26

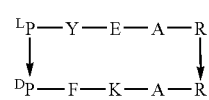

26

By a procedure analogous to that described in Example 1, Fmoc-Ala-OH, Fmoc-Glu(OtBu)-OH, Fmoc-Tyr(tBu)-OH, Fmoc-$^L$Pro-OH, Fmoc-$^D$Pro-OH, Fmoc-Phe-OH, Fmoc-Lys(Boc)-OH, Fmoc-Ala-OH and Fmoc-Arg(Pmc)-OH were coupled to the Fmoc-Arg(Pmc)-OH loaded resin, cleaved, cyclised and deprotected to yield compound 26 [SEQ ID NO:59].

| MW: | $C_{57}H_{85}N_{17}O_{13}$, [1216.41] |
|---|---|
| MS(ESI): | 608.8 $[M + 2H^+]^{2+}$ |
| HPLC-RT(min.): | 8.27 |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 27

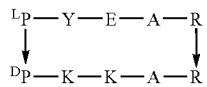

27

By a procedure analogous to that described in Example 1, Fmoc-Ala-OH, Fmoc-Glu(OtBu)-OH, Fmoc-Tyr(tBu)-OH, Fmoc-$^L$Pro-OH, Fmoc-$^D$Pro-OH, Fmoc-Lys(Boc)-OH, Fmoc-Lys(Boc)-OH, Fmoc-Ala-OH and Fmoc-Arg(Pmc)-OH were coupled to the Fmoc-Arg(Pmc)-OH loaded resin, cleaved, cyclised and deprotected to yield compound 27 [SEQ ID NO:60].

| MW: | $C_{54}H_{88}N_{18}O_{13}$, [1197.4] |
|---|---|
| MS(ESI): | 599.4 $[M + 2H^+]^{2+}$ |
| HPLC-RT(min.): | 8.85 |
| Conditions: | Analytical HPLC-conditions: column CC 250/4 Nucleosil 100-5 Protect 1 (Ser. No. 8111346, Batch 8023); gradient 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 28

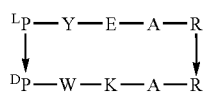

28

By a procedure analogous to that described in Example 1, Fmoc-Ala-OH, Fmoc-Glu(OtBu)-OH, Fmoc-Tyr(tBu)-OH, Fmoc-$^L$Pro-OH, Fmoc-$^D$Pro-OH, Fmoc-Trp(Boc)-OH, Fmoc-Lys(Boc)-OH, Fmoc-Ala-OH and Fmoc-Arg(Pmc)-OH were coupled to the Fmoc-Arg(Pmc)-OH loaded resin, cleaved, cyclised and deprotected to yield compound 28 [SEQ ID NO:61].

| MW: | $C_{59}H_{87}N_{18}O_{13}$, [1256.4] |
|---|---|
| MS(ESI): | 628.50 $[M + 2H^+]^{2+}$, 419.20 $[M + 3H^+]^{3+}$ |
| HPLC-RT(min.): | 9.16 |
| Conditions: | Analytical HPLC-conditions: column CC 250/4 Nucleosil 100-5 Protect 1 (Ser. No. 8111346, Batch 8023); gradient 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 29

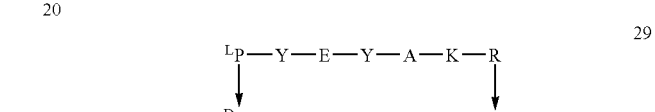

29

By a procedure analogous to that described in Example 1, Fmoc-Lys(Boc)-OH, Fmoc-Ala-OH, Fmoc-Tyr(OtBu)-OH, Fmoc-Glu(OtBu)-OH, Fmoc-Tyr(tBu)-OH, Fmoc-$^L$Pro-OH, Fmoc-$^D$Pro-OH, Fmoc-Tyr(tBu)-OH, Fmoc-Lys(Boc)-OH, Fmoc-Tyr(tBu)-OH, Fmoc-Ala-OH, Fmoc-Glu(OtBu)-OH and Fmoc-Arg(Pmc)-OH were coupled to the Fmoc-Arg(Pmc)-OH loaded resin, cleaved, cyclised and deprotected to yield compound 29 [SEQ ID NO:62].

| MW: | $C_{86}H_{122}N_{22}O_{22}$, [1816] |
|---|---|
| MS(ESI): | 908 $[M + 2H^+]^{2+}$, 606.2 $[M + 3H^+]^{3+}$ |
| HPLC-RT(min.): | 8.40 |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 30

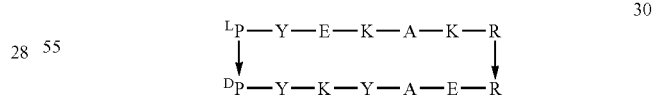

30

By a procedure analogous to that described in Example 1, Fmoc-Lys(Boc)-OH, Fmoc-Ala-OH, Fmoc-Lys(Boc)-OH, Fmoc-Glu(OtBu)-OH, Fmoc-Tyr(tBu)-OH, Fmoc-$^L$Pro-OH, Fmoc-$^D$Pro-OH, Fmoc-Tyr(tBu)-OH, Fmoc-Lys(Boc)-OH, Fmoc-Tyr(tBu)-OH, Fmoc-Ala-OH, Fmoc-Glu(OtBu)-OH and Fmoc-Arg(Pmc)-OH were coupled to the Fmoc-Arg(Pmc)-OH loaded resin, cleaved, cyclised and deprotected to yield compound 30 [SEQ ID NO:63].

MW:                C$_{83}$H$_{125}$N$_{23}$O$_{21}$, [1781]
MS(ESI):           594.6 [M + 3H$^+$]$^{3+}$
HPLC-RT(min.):     9.04
Conditions:        Analytical HPLC-conditions: column CC 250/4
                   Nucleosil 100-5 Protect 1 (Ser. No. 8111346,
                   Batch 8023); gradient: 10% acetonitril/90%
                   water(containing 0.1% trifluoroacetic acid)
                   to 100% acetonitril in 15 minutes; stay
                   constant for 4 minutes and return to 10%
                   acetonitril/water(0.1% trifluoroacetic
                   acid) in 4 minutes.

EXAMPLE 31

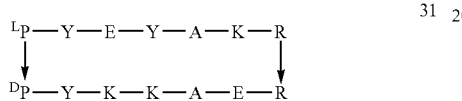

By a procedure analogous to that described in Example 1, Fmoc-Lys(Boc)-OH, Fmoc-Ala-OH, Fmoc-Tyr(tBu)-OH, Fmoc-Glu(OtBu)-OH, Fmoc-Tyr(tBu)-OH, Fmoc-$^L$Pro-OH, Fmoc-$^D$Pro-OH, Fmoc-Tyr(tBu)-OH, Fmoc-Lys(Boc)-OH, Fmoc-Lys(Boc)-OH, Fmoc-Ala-OH, Fmoc-Glu(OtBu)-OH and Fmoc-Arg(Pmc)-OH were coupled to the Fmoc-Arg(Pmc)-OH loaded resin, cleaved, cyclised and deprotected to yield compound 31 [SEQ ID NO:64]

MW:                C$_{83}$H$_{125}$N$_{23}$O$_{21}$, [1721]
MS(ESI):           891.15 [M + 2H$^+$]$^{2+}$, 594.85 [M + 3H$^+$]$^{3+}$
HPLC-RT(min.):     9.84
Conditions:        Analytical HPLC-conditions: column CC 250/4
                   Nucleosil 100-5 Protect 1 (Ser. No. 8111346,
                   Batch 8023); gradient: 10% acetonitril/90%
                   water(containing 0.1% trifluoroacetic acid)
                   to 100% acetonitril in 15 minutes; stay
                   constant for 4 minutes and return to 10%
                   acetonitril/water(0.1% trifluoroacetic
                   acid) in 4 minutes.

EXAMPLE 32

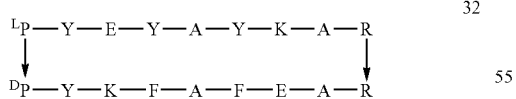

By a procedure analogous to that described in Example 1, Fmoc-Ala-OH, Fmoc-Lys(Boc)-OH, Fmoc-Tyr(tBu)-OH, Fmoc-Ala-OH, Fmoc-Tyr(tBu)-OH, Fmoc-Glu(OtBu)-OH, Fmoc-Tyr(tBu)-OH, Fmoc-$^L$Pro-OH, Fmoc-$^D$Pro-OH, Fmoc-Tyr(tBu)-H, Fmoc-Lys(Boc)-OH, Fmoc-Phe-OH, Fmoc-Ala-OH, Fmoc-Phe-OH, Fmoc-Glu(OtBu)-OH, Fmoc-Ala-OH, and Fmoc-Arg(Pmc)-OH were coupled to the Fmoc-Arg(Pmc)-OH loaded resin, cleaved, cyclised and deprotected to yield compound 32 [SEQ ID NO:65]

MW:                C$_{110}$H$_{150}$N$_{26}$O$_{26}$, [2252.4]
MS(ESI):           751.93 [M + 3H$^+$]$^{3+}$
HPLC-RT(min.):     9.42
Conditions:        Analytical HPLC-conditions: column CC 250/4
                   Nucleosil 100-5 Protect 1 (Ser. No. 8111346,
                   Batch 8023); gradient: 10% acetonitril/90%
                   water(containing 0.1% trifluoroacetic acid)
                   to 100% acetonitril in 15 minutes; stay
                   constant for 4 minutes and return to 10%
                   acetonitril/water(0.1% trifluoroacetic
                   acid) in 4 minutes.

EXAMPLE 33

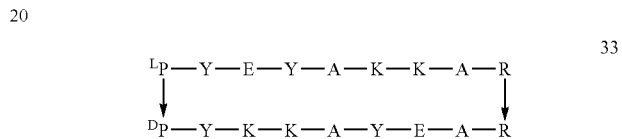

By a procedure analogous to that described in Example 1, Fmoc-Ala-OH, Fmoc-Lys(Boc)-OH, Fmoc-Lys(Boc)-OH, Fmoc-Ala-OH, Fmoc-Tyr(tBu)-OH, Fmoc-Glu(OtBu)-OH, Fmoc-Tyr(tBu)-OH, Fmoc-$^L$Pro-OH, Fmoc-$^D$Pro-OH, Fmoc-Tyr(tBu)-OH, Fmoc-Lys(Boc)-OH, Fmoc-Lys(Boc)-OH, Fmoc-Ala-OH, Fmoc-Tyr(tBu)-OH, Fmoc-Glu(OtBu)-OH, Fmoc-Ala-OH, and Fmoc-Arg(Pmc)-OH were coupled to the Fmoc-Arg(Pmc)-OH loaded resin, cleaved, cyclised and deprotected to yield compound 33 [SEQ ID NO:66].

MW:                C$_{104}$H$_{156}$N$_{28}$O$_{26}$, [2214.5]
MS(ESI):           738.10 [M + 3H$^+$]$^{3+}$
HPLC-RT(min.):     13.46
Conditions:        Analytical HPLC-conditions: column CC 250/4
                   Nucleosil 100-5 Protect 1 (Ser. No. 8111346,
                   Batch 8023); gradient 10% acetonitril/90%
                   water(containing 0.1% trifluoroacetic acid)
                   to 100% acetonitril in 15 minutes; stay
                   constant for 4 minutes and return to 10%
                   acetonitril/water(0.1% trifluoroacetic
                   acid) in 4 minutes.

EXAMPLE 34

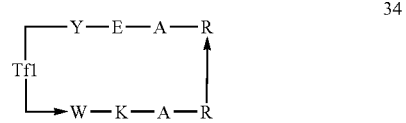

By a procedure analogous to that described in Example 1, Fmoc-Ala-OH, Fmoc-Glu(OtBu)-OH, Fmoc-Tyr(tBu)-OH, Template f1, Fmoc-Tyr(tBu)-OH, Fmoc-Lys-(Boc)-OH, Fmoc-Ala-OH, and Fmoc-Arg(Pmc)-OH were coupled to the Fmoc-Arg(Pmc)-OH loaded resin, cleaved, cyclised and deprotected to yield compound 34 [SEQ ID NO:67].

| | |
|---|---|
| MW: | C₆₇H₉₁N₁₆O₁₆, [1376.5] |
| MS(ESI): | 689.02 [M + 2H⁺]²⁺ |
| HPLC-RT(min.): | 9.87 |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water (0.1% trifluoroacetic acid) in 4 minutes. |

EXAMPLE 35

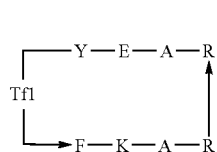

35

By a procure analogous to that described in Example 1, Fmoc-Ala-OH, Fmoc-Glu(OtBu)-OH, Fmoc-Tyr(tBu)-OH, Template f1, Fmoc-Phe-OH, Fmoc-Lys(Boc)-OH, Fmoc-Ala-OH, and Fmoc-Arg(Pmc)-OH were coupled to the Fmoc-Arg(Pmc)-OH loaded resin, cleaved, cyclised and deprotected to yield compound 35 [SEQ ID NO:68].

| | |
|---|---|
| MW: | C₆₇H₉₁N₁₆O₁₅, [1360.14] |
| MS(ESI): | 681.44 [M + 2H⁺]²⁺, 454.77 [M + 3H⁺]³⁺ |
| HPLC-RT(min.): | 9.68 |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 36

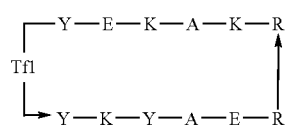

36

By a procedure analogous to that described in Example 1, Fmoc-Lys(Boc)-OH, Fmoc-Ala-OH, Fmoc-Lys(Boc)-OH, Fmoc-Glu(OtBu)-OH, Fmoc-Tyr(tBu)-OH, Template f1, Fmoc-Tyr(tBu)-OH, Fmoc-Lys(Boc)-OH, Fmoc-Tyr(tBu)-OH, Fmoc-Ala-OH, Fmoc-Glu(OtBu)-OH, and Fmoc-Arg(Pmc)-OH were coupled to the Fmoc-Arg(Pmc)-OH loaded resin, cleaved, cyclised and deprotected to yield compound 36 [SEQ ID NO:69].

| | |
|---|---|
| MW: | C₉₃H₁₃₁N₂₂O₂₃, [1925.19] |
| MS(ESI): | 64328 [M + 3H⁺]³⁺ |
| HPLC-RT(min.): | 8.85 min. |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 37

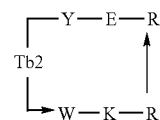

37

By a procedure analogous to that described in Example 1, Fmoc-Glu(OtBu)-OH, Fmoc-Tyr(tBu)-OH, Template b1, Fmoc-Trp(Boc)-OH, Fmoc-Lys(Boc)-OH and Fmoc-Arg(Pmc)-OH were coupled to the Fmoc-Arg(Pmc)-OH loaded resin, cleaved, cyclised and deprotected to yield compound 37 [SEQ ID NO:70].

| | |
|---|---|
| MW: | C₅₄H₇₄N₁₇O₁₄, [1185.18] |
| MS(ESI): | 593.83 [M + 2H⁺]²⁺ |
| HPLC-RT(min.): | 11.23 |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 38

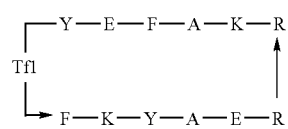

38

By a procedure analogous to that described in Example 1, Fmoc-Lys(Boc)-OH, Fmoc-Ala-OH, Fmoc-Phe-OH, Fmoc-Tyr(tBu)-OH, Fmoc-Glu(OtBu)-OH, Fmoc-Tyr(tBu)-OH, Template f1, Fmoc-Phe-OH, Fmoc-Lys(Boc)-OH, Fmoc-Tyr(OtBu)-OH, Fmoc-Ala-OH, Fmoc-Glu(OtBu)-OH and Fmoc-Arg(Pmc)-OH were coupled to the Fmoc-Arg(Pmc)-OH loaded resin, cleaved, cyclised and deprotected to yield compound 38 [SEQ ID NO:71].

| | |
|---|---|
| MW: | $C_{96}H_{129}N_{21}O_{22}$, [1929.23] |
| MS(ESI): | 644 $[M + 3H^+]^{3+}$, 483.11 $[M + 4H^+]^{4+}$ |
| HPLC-RT(min.): | 9.22 |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 39

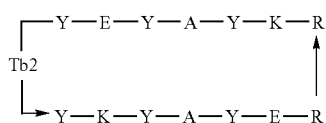

By a procedure analogous to that described in Example 1, Fmoc-Lys(Boc)-OH Fmoc-Tyr(tBu)-OH Fmoc-Ala-OH, Fmoc-Tyr(tBu)-OH, Fmoc-Glu(OtBu)-OH, Fmoc-Tyr(tBu)-OH, Template b1, Fmoc-Tyr(tBu)-OH, Fmoc-Lys(Boc)-OH, Fmoc-Tyr(OtBu)-OH, Fmoc-Ala-OH, Fmoc-Tyr(tBu)-OH, Fmoc-Glu(OtBu)-OH and Fmoc-Arg(Pmc)-OH were coupled to the Fmoc-Arg(Pmc)-OH loaded resin, cleaved, cyclised and deprotected to yield compound 39 [SEQ ID NO:72].

| | |
|---|---|
| MW: | $C_{105}H_{138}N_{25}O_{29}$, [2214.3] |
| MS(ESI): | 737.76 $[M + 3H^+]^{3+}$ |
| HPLC-RT(min.): | 13.26 |
| Conditions: | Analytical HPLC-conditions: column CC 250/4 Nucleosil 100-5 Protect 1 (Ser. No. 8111346, Batch 8023); gradient: 10% acetonitril/90% water(containing 0.1% trifluoroacetic acid) to 100% acetonitril in 15 minutes; stay constant for 4 minutes and return to 10% acetonitril/water(0.1% trifluoroacetic acid) in 4 minutes. |

EXAMPLE 40

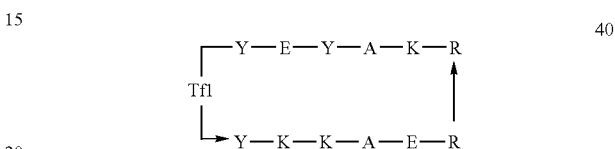

By a procedure analogous to that described in Example 1, Fmoc-Lys(Boc)-OH, Fmoc-Ala-OH, Fmoc-Tyr(tBu)-OH, Fmoc-Glu(OtBu)-OH, Fmoc-Tyr(tBu)-OH, Template f1, Fmoc-Tyr(tBu)-OH, Fmoc-Lys(Boc)-OH, Fmoc-Lys(Boc)-OH, Fmoc-Ala-OH, Fmoc-Glu(OtBu)-OH and Fmoc-Arg(Pmc)-OH were coupled to the Fmoc-Arg(Pmc)-OH loaded resin, cleaved, cyclised and deprotected to yield compound 40 [SEQ ID NO:73].

| | |
|---|---|
| MW: | $C_{93}H_{131}N_{22}O_{23}$, [1926.22] |
| MS( ESI): | 643.01 $[M + 3H^+]^{3+}$, 482.35 $[M + 4H^+]^{4+}$ |
| HPLC-RT (min.): | 8.99 |
| Conditions: | Analytical HPLC-conditions: column CC 250/4 Nucleosil 100-5 Protect 1 (Ser. No. 8111346, Batch 8023); gradient: 10% acetonitril / 90% water (containing 0.1% trifluoroacetic acid) to 100% acetonitril in 15 minutes; stay constant for 4 minutes and return to 10% acetonitril / water (0.1% trifluoroacetic acid) in 4 minutes. |

What is claimed is:

1. A process for the manufacture of a library of numerous compounds of the general formula

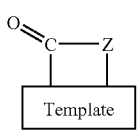

I wherein

Z is a chain of n α-amino acid residues which, if their α-C atom is asymmetric, have L-configuration, n being an integer from 4 to 20, the positions of said amino acid residues in said chain being counted starting from the N-terminal amino acid;

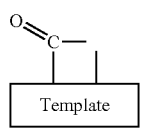

is one of the groups of formulae

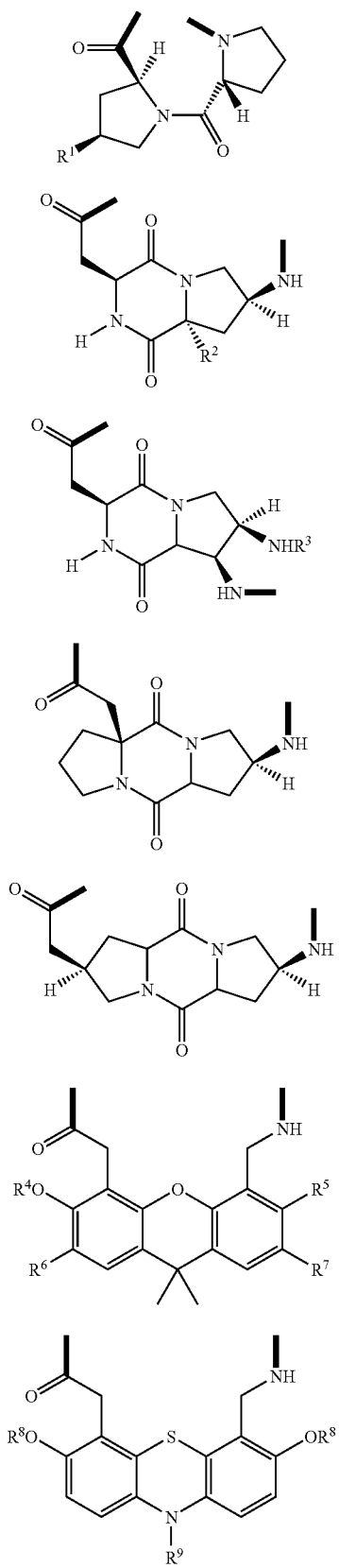

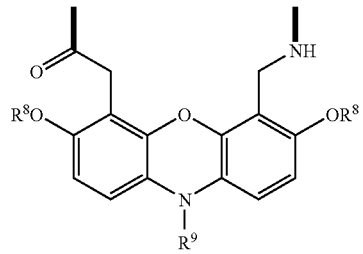

R[1] is hydrogen or a protected amino group;
R[2] is hydrogen or a group of formula $CH_2$—$COOR^{10}$;
R[3] is an amino-protecting group;
R[4] is lower alkyl or aryl-lower alkyl;
R[5] is lower alkyl, lower alkoxy or aryl;
R[6] is hydrogen, lower alkyl, substituted lower alkyl, aryl, Br or $NO_2$;
R[7] is hydrogen, lower alkyl, substituted lower alkyl, aryl, Br or $NO_2$;
R[8] is lower alkyl, substituted lower alkyl or aryl-lower alkyl;
R[9] is lower alkyl, substituted lower alkyl or aryl-lower alkyl; and
R[10] is hydrogen, lower alkyl, substituted lower alkyl, aryl, aryl-lower alkyl, aroyl-lower alkyl or allyl;

and of salts thereof, which process is carried out as parallel array synthesis to yield a library of numerous compounds of formula I, and which process comprises (a) coupling a solid support derived from polystyrene crosslinked with divinylbenzene which is functionalized by means of a 2-chlorotrityl linker with an appropriately N-protected derivative of that amino acid which in the desired end-product is in position n/2, n/2+1 or n/2−1 if n is an even number and, respectively, in position n/2+½ or n/2−½ if n is an odd number, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating, if necessary, steps (c) and (d) until the N-terminal amino acid residue has been introduced;

(f) coupling the product thus obtained with a compound of the general formula

II wherein

-continued

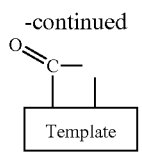

is as defined above and X is an N-protecting group or, if

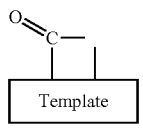

is to be group (a), above, alternatively (fa) coupling the product obtained in step (d) or (e) with a compound of the general formula III

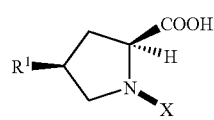

wherein $R^1$ and X are as defined above;

(fb) removing the N-protecting group from the product thus obtained; and (fc) coupling the product thus obtained with an appropriately N-protected derivative of D-proline;

(g) removing the N-protecting group from the product obtained in step (f) or (fc);

(h) coupling the product thus obtained with an appropriately N-protected derivative of that amino acid which in the desired end-product is in position n, any functional group which may be present in said N-protected amino acid derivative being likewise appropriately protected;

(i) removing the N-protecting group from the product thus obtained;

(j) coupling the product thus obtained with an appropriately N-protected derivative of that amino acid which in the desired end-product is one position farther away from position n, any functional group which may be present in said N-protected amino acid derivative being likewise appropriately protected;

(k) removing the N-protecting group from the product thus obtained;

(l) repeating, if necessary, steps (j) and (k) until all amino acid residues have been introduced;

(m) detaching the product thus obtained from the solid support;

(n) cyclising the product cleaved from the solid support by means of O-(7-azabenzotriazol-1-yl)-N,N,N',N'-tetramethyluronium hexafluorophosphate ("HATU")/7-aza-1-hydroxybenzotriazole ("HOAt");

(o) removing any protecting groups present on functional groups of any members of the chain of amino acid residues and, if desired, any protecting group(s) which may in addition be present in the molecule.

2. A modification of the process according to claim 1 for the manufacture of a library of numerous enantiomers of the compounds of formula I as defined in claim 1 in which all amino acids which have an asymmetric α-carbon atom are used in their D-Form and the enantiomer of a template corresponding to structure (a), (b), (c), (d) or (e) or a template corresponding to formula (f), (g) or (h) is used in step (f) and, respectively, the enantiomer of a compound of formula III is used in step (fa) and a derivative of L-proline is used in step (fc).

3. A process according to claim 1, wherein the library comprises 24 to 192 compounds.

4. A process according to claim 2, wherein the library comprises 24 to 192 compounds.

5. A process according to claim 3, wherein the library comprises 96 compounds.

6. A process according to claim 4, wherein the library comprises 96 compounds.

7. A library of numerous compounds of formula I as defined in claim 1, obtainable by the process according to claim 1.

8. A library of numerous enantiomers of the compounds of formula I as defined in claim 1, obtainable by the process according to claim 2.

9. A library according to claim 7, comprising 24 to 192 compounds, obtainable by the process according to claim 3.

10. A library according to claim 8, comprising 24 to 192 compounds, obtainable by the process according to claim 4.

11. A library according to claim 9, comprising 96 compounds, obtainable by the process according to claim 5.

12. A library according to claim 10, comprising 96 compounds, obtainable by the process according to claim 6.

* * * * *

UNITED STATES PATENT AND TRADEMARK OFFICE
CERTIFICATE OF CORRECTION

PATENT NO. : 7,091,313 B2  
APPLICATION NO. : 11/029331  
DATED : August 15, 2006  
INVENTOR(S) : Robinson et al.

It is certified that error appears in the above-identified patent and that said Letters Patent is hereby corrected as shown below:

On Title Page
At (74) Attorney, Agent, or Firm, the printed patent should read --Hoffmann & Baron, LLP--.

At column 8, line 65, the printed patent should read --...formulae (a), (e), (f), (g) and (h).--.

Signed and Sealed this

Fifth Day of December, 2006

JON W. DUDAS  
*Director of the United States Patent and Trademark Office*

SEQUENCE LISTING

<160> NUMBER OF SEQ ID NOS: 73

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Key Sequence

<400> SEQUENCE: 1

Val Arg Lys Lys
 1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:Key Sequence -continued

```
<400> SEQUENCE: 2

Lys Lys Tyr Leu
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:Key Sequence

<400> SEQUENCE: 3

Trp Leu Asp Val
  1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:Key Sequence

<400> SEQUENCE: 4

Tyr Ile Arg Leu Pro
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:Key Sequence

<400> SEQUENCE: 5

Tyr Ile Gly Ser Arg
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:Key Sequence

<400> SEQUENCE: 6

Ile Lys Val Ala Val
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:Key Sequence
<220> FEATURE:
<223> OTHER INFORMATION: residues 4 and 5 unspecified

<400> SEQUENCE: 7

Pro Pro Arg Xaa Xaa Trp
  1               5

<210> SEQ ID NO 8
<211> LENGTH: 10
<212> TYPE: PRT
<213> ORGANISM: Artificial Sequence
<220> FEATURE:
```

-continued

```
<223> OTHER INFORMATION: Description of Artificial Sequence:Key Sequence
<300> PUBLICATION INFORMATION:

<400> SEQUENCE: 8

Ile Tyr Tyr Lys Asp Gly Ala Leu Lys Tyr
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 9

Val Lys Asn Tyr Gly Val Lys Asn Ser Glu Trp Ile
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Peptide
      Fragment

<400> SEQUENCE: 10

Val Lys Asn Tyr Gly Val Lys Asn Ser Glu Trp Thr
 1               5                  10

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 11

Gly Arg Gly Asp
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 12

Arg Gly Asp Gly
 1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 13

Phe Tyr Thr Gly Thr
 1               5
```

```
<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 14

Tyr Arg Asp Ala Met
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 15

Asn Thr Tyr Ser Gly Val
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 16

Trp Asp Asp Gly Ser Asp
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 17

Leu Trp Tyr Ser Asn His Trp Val
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 18

Ala Asn Pro Asn Ala Ala
 1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 19
```

```
Ala Arg Gly Asp
  1

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 20

Val Ala Ala Phe Leu Ala Leu Ala
  1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 21

Arg Gly Asp Val
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 22

Ala Thr Val Gly
  1

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 23

Glu Arg Gly Asp Val Tyr
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 24

Ile Ala Arg Gly Asp Phe Pro Asp
  1               5

<210> SEQ ID NO 25
<211> LENGTH: 12
<212> TYPE: PRT
<213> ORGANISM: Artificial Sequence
```

```
<220> FEATURE:
<223> OTHER INFORMATION: Description of Artificial Sequence:Peptide
      Fragment

<400> SEQUENCE: 25

Ala Arg Ile Ala Arg Gly Asp Phe Pro Asp Asp Arg
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 26

Ala Arg Gly Asp Phe Pro
1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 27

Arg Gly Asp Phe
1

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 28

Arg Ile Ala Arg Gly Asp Phe Pro Asp Asp
1               5                   10

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 29

Gly Gly Ala Gly
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:Peptide
      Fragment

<400> SEQUENCE: 30

Gly Asp Gly Gly
1
```

```
<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence:Protected
      Peptide Fragment
<220> FEATURE:
<223> OTHER INFORMATION: residues 1 and 2 are Lys(Boc); residue 5 is
      D-Pro; residue 7 is Glu(OtBu); residue 10 is Arg(Pmc)

<400> SEQUENCE: 31

Xaa Xaa Pro Ile Xaa Pro Xaa Ile Val Xaa
 1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:Cyclic
      Peptide
<220> FEATURE:
<223> OTHER INFORMATION: residue 10 is D-Pro

<400> SEQUENCE: 32

Pro Glu Ile Val Arg Lys Lys Pro Ile Xaa
 1               5                   10

<210> SEQ ID NO 33
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 33

Pro Glu Tyr Val Arg Lys Lys Tyr Ile Xaa
 1               5                   10

<210> SEQ ID NO 34
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 34

Pro Glu Trp Val Arg Lys Lys Trp Ile Xaa
 1               5                   10

<210> SEQ ID NO 35
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 35

Pro Glu Ala Val Arg Lys Lys Ala Ile Xaa
```

<210> SEQ ID NO 36
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 36

Pro Glu Ser Val Arg Lys Lys Ser Ile Xaa
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: residue 2 is Glu, Tyr, Trp, Ala; residue 3 is
      Ile, Tyr, Trp, Ala, Ser, Lys; residue 8 is Pro, Tyr, Trp, Ala,
      Ser, Lys; residue 9 is Ile, Tyr, Trp, Ala; residue 10 is D-Pro
<220> FEATURE:
<223> OTHER INFORMATION: Description of Artificial Sequence:Cyclic
      Peptide

<400> SEQUENCE: 37

Pro Xaa Xaa Val Arg Lys Lys Xaa Xaa Xaa
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 38

Pro Glu Lys Val Arg Lys Lys Ile Lys Xaa
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 39

Pro Tyr Ile Val Arg Lys Lys Pro Tyr Xaa
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

```
<400> SEQUENCE: 40

Pro Tyr Tyr Val Arg Lys Lys Tyr Tyr Xaa
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 41

Pro Tyr Trp Val Arg Lys Lys Trp Tyr Xaa
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence:Cyclic
      Peptide
<220> FEATURE:
<223> OTHER INFORMATION: residue 10 is D-Pro

<400> SEQUENCE: 42

Pro Tyr Ala Val Arg Lys Lys Ala Tyr Xaa
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 43

Pro Tyr Ser Val Arg Lys Lys Ser Tyr Xaa
 1               5                  10

<210> SEQ ID NO 44
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 44

Pro Tyr Lys Val Arg Lys Lys Lys Tyr Xaa
 1               5                  10

<210> SEQ ID NO 45
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide
```

```
<400> SEQUENCE: 45

Pro Trp Ile Val Arg Lys Lys Pro Trp Xaa
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 46

Pro Trp Tyr Val Arg Lys Lys Tyr Trp Xaa
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 47

Pro Trp Trp Val Arg Lys Lys Trp Trp Xaa
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 48

Pro Trp Ala Val Arg Lys Lys Ala Trp Xaa
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 49

Pro Trp Ser Val Arg Lys Lys Ser Trp Xaa
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
```

Peptide

<400> SEQUENCE: 50

Pro Trp Lys Val Arg Lys Lys Lys Trp Xaa
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 51

Pro Ala Ile Val Arg Lys Lys Pro Ala Xaa
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 52

Pro Ala Tyr Val Arg Lys Lys Tyr Ala Xaa
 1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence:Cyclic
      Peptide
<220> FEATURE:
<223> OTHER INFORMATION: residue 10 is D-Pro

<400> SEQUENCE: 53

Pro Ala Trp Val Arg Lys Lys Trp Ala Xaa
 1               5                  10

<210> SEQ ID NO 54
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 54

Pro Ala Ala Val Arg Lys Lys Ala Ala Xaa
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: residue 10 is D-Pro
<220> FEATURE:

-continued

<223> OTHER INFORMATION: Description of Artificial Sequence:Cyclic
      Peptide

<400> SEQUENCE: 55

Pro Ala Ser Val Arg Lys Lys Ser Ala Xaa
 1               5                  10

<210> SEQ ID NO 56
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Key Sequence

<400> SEQUENCE: 56

Pro Ala Lys Val Arg Lys Lys Lys Ala Xaa
 1               5                  10

<210> SEQ ID NO 57
<211> LENGTH: 5
<212> TYPE: PRT
<213> ORGANISM: Artificial Sequence
<220> FEATURE:
<223> OTHER INFORMATION: residue 1 is Lys; residue 2 is Tyr, Phe, Lys,
      Trp; residue 3 is template; residue 4 is Tyr; residue 5 is Glu
<220> FEATURE:
<223> OTHER INFORMATION: Description of Artificial Sequence:Peptide
      Fragment

<400> SEQUENCE: 57

Xaa Xaa Xaa Xaa Xaa
 1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence:Cyclic
      Peptide
<220> FEATURE:
<223> OTHER INFORMATION: residue 10 is D-Pro

<400> SEQUENCE: 58

Pro Tyr Glu Ala Arg Arg Ala Lys Tyr Xaa
 1               5                  10

<210> SEQ ID NO 59
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 59

Pro Tyr Glu Ala Arg Arg Ala Lys Phe Xaa
 1               5                  10

<210> SEQ ID NO 60
<211> LENGTH: 10
<212> TYPE: PRT
<213> ORGANISM: Artificial Sequence
<220> FEATURE:
<223> OTHER INFORMATION: residue 10 is D-Pro

```
<220> FEATURE:
<223> OTHER INFORMATION: Description of Artificial Sequence:Cyclic
      Peptide

<400> SEQUENCE: 60

Pro Tyr Glu Ala Arg Arg Ala Lys Lys Xaa
 1               5                  10

<210> SEQ ID NO 61
<211> LENGTH: 10
<212> TYPE: PRT
<213> ORGANISM: Artificial Sequence
<220> FEATURE:
<223> OTHER INFORMATION: residue 10 is D-Pro
<220> FEATURE:
<223> OTHER INFORMATION: Description of Artificial Sequence:Cyclic
      Peptide

<400> SEQUENCE: 61

Pro Tyr Glu Ala Arg Arg Ala Lys Trp Xaa
 1               5                  10

<210> SEQ ID NO 62
<211> LENGTH: 14
<212> TYPE: PRT
<213> ORGANISM: Artificial Sequence
<220> FEATURE:
<223> OTHER INFORMATION: residue 14 is D-Pro
<220> FEATURE:
<223> OTHER INFORMATION: Description of Artificial Sequence:Cyclic
      Peptide

<400> SEQUENCE: 62

Pro Tyr Glu Tyr Ala Lys Arg Arg Glu Ala Tyr Lys Tyr Xaa
 1               5                  10

<210> SEQ ID NO 63
<211> LENGTH: 14
<212> TYPE: PRT
<213> ORGANISM: Artificial Sequence
<220> FEATURE:
<223> OTHER INFORMATION: residue 14 is D-Pro
<220> FEATURE:
<223> OTHER INFORMATION: Description of Artificial Sequence:Cyclic
      Peptide

<400> SEQUENCE: 63

Pro Tyr Glu Lys Ala Lys Arg Arg Glu Ala Tyr Lys Tyr Xaa
 1               5                  10

<210> SEQ ID NO 64
<211> LENGTH: 14
<212> TYPE: PRT
<213> ORGANISM: Artificial Sequence
<220> FEATURE:
<223> OTHER INFORMATION: residue 14 is D-Pro
<220> FEATURE:
<223> OTHER INFORMATION: Description of Artificial Sequence:Cyclic
      Peptide

<400> SEQUENCE: 64

Pro Tyr Glu Tyr Ala Lys Arg Arg Glu Ala Lys Lys Tyr Xaa
 1               5                  10

<210> SEQ ID NO 65
<211> LENGTH: 18
<212> TYPE: PRT
<213> ORGANISM: Artificial Sequence
<220> FEATURE:
```

```
<223> OTHER INFORMATION: residue 18 is D-Pro
<220> FEATURE:
<223> OTHER INFORMATION: Description of Artificial Sequence:Cyclic
      Peptide

<400> SEQUENCE: 65

Pro Tyr Glu Tyr Ala Tyr Lys Ala Arg Arg Ala Glu Phe Ala Phe Lys
 1               5                  10                  15

Tyr Xaa

<210> SEQ ID NO 66
<211> LENGTH: 18
<212> TYPE: PRT
<213> ORGANISM: Artificial Sequence
<220> FEATURE:
<223> OTHER INFORMATION: residue 18 is D-Pro
<220> FEATURE:
<223> OTHER INFORMATION: Description of Artificial Sequence:Cyclic
      Peptide

<400> SEQUENCE: 66

Pro Tyr Glu Tyr Ala Lys Lys Ala Arg Arg Ala Glu Tyr Ala Lys Lys
 1               5                  10                  15

Tyr Xaa

<210> SEQ ID NO 67
<211> LENGTH: 9
<212> TYPE: PRT
<213> ORGANISM: Artificial Sequence
<220> FEATURE:
<223> OTHER INFORMATION: residue 9 is Template f1
<220> FEATURE:
<223> OTHER INFORMATION: Description of Artificial Sequence:Cyclic
      Template-fixed Peptide

<400> SEQUENCE: 67

Tyr Glu Ala Arg Arg Ala Lys Tyr Xaa
 1               5

<210> SEQ ID NO 68
<211> LENGTH: 9
<212> TYPE: PRT
<213> ORGANISM: Artificial Sequence
<220> FEATURE:
<223> OTHER INFORMATION: residue 9 is Template f1
<220> FEATURE:
<223> OTHER INFORMATION: Description of Artificial Sequence:Cyclic
      Template-fixed Peptide

<400> SEQUENCE: 68

Tyr Glu Ala Arg Arg Ala Lys Phe Xaa
 1               5

<210> SEQ ID NO 69
<211> LENGTH: 13
<212> TYPE: PRT
<213> ORGANISM: Artificial Sequence
<220> FEATURE:
<223> OTHER INFORMATION: residue 13 is Template f1
<220> FEATURE:
<223> OTHER INFORMATION: Description of Artificial Sequence:Cyclic
      Template-fixed Peptide

<400> SEQUENCE: 69

Tyr Glu Lys Ala Lys Arg Arg Glu Ala Tyr Lys Tyr Xaa
 1               5                  10
```

-continued

```
<210> SEQ ID NO 70
<211> LENGTH: 7
<212> TYPE: PRT
<213> ORGANISM: Artificial Sequence
<220> FEATURE:
<223> OTHER INFORMATION: residue 7 is Template b2
<220> FEATURE:
<223> OTHER INFORMATION: Description of Artificial Sequence:Cyclic
      Template-fixed Peptide

<400> SEQUENCE: 70

Tyr Glu Arg Arg Lys Trp Xaa
  1               5

<210> SEQ ID NO 71
<211> LENGTH: 13
<212> TYPE: PRT
<213> ORGANISM: Artificial Sequence
<220> FEATURE:
<223> OTHER INFORMATION: residue 13 is Template f1
<220> FEATURE:
<223> OTHER INFORMATION: Description of Artificial Sequence:Cyclic
      Template-fixed Peptide

<400> SEQUENCE: 71

Tyr Glu Phe Ala Lys Arg Arg Glu Ala Tyr Lys Phe Xaa
  1               5                  10

<210> SEQ ID NO 72
<211> LENGTH: 15
<212> TYPE: PRT
<213> ORGANISM: Artificial Sequence
<220> FEATURE:
<223> OTHER INFORMATION: residue 15 is Template b2
<220> FEATURE:
<223> OTHER INFORMATION: Description of Artificial Sequence:Cyclic
      Template-fixed Peptide

<400> SEQUENCE: 72

Tyr Glu Tyr Ala Tyr Lys Arg Arg Glu Tyr Ala Tyr Lys Tyr Xaa
  1               5                  10                  15

<210> SEQ ID NO 73
<211> LENGTH: 13
<212> TYPE: PRT
<213> ORGANISM: Artificial Sequence
<220> FEATURE:
<223> OTHER INFORMATION: residue 13 isTemplate f1
<220> FEATURE:
<223> OTHER INFORMATION: Description of Artificial Sequence:Cyclic
      Template-fixed Peptide

<400> SEQUENCE: 73

Tyr Glu Tyr Ala Lys Arg Arg Glu Ala Lys Lys Tyr Xaa
  1               5                  10
```